(12) United States Patent
Schell et al.

(10) Patent No.: US 9,916,772 B1
(45) Date of Patent: Mar. 13, 2018

(54) ATOMIC AND MOLECULAR MODELING SYSTEM

(71) Applicant: Schell Games LLC, Pittsburgh, PA (US)

(72) Inventors: Jesse N. Schell, Pittsburgh, PA (US); Michael Lee, Pittsburgh, PA (US); Yotam Haimberg, Pittsburgh, PA (US); William R. Ball, Gibsonia, PA (US); Anisha Deshmane, Pittsburgh, PA (US); Adam Lippmann, Pittsburgh, PA (US); Chris Patlovany, Aliso Viejo, CA (US)

(73) Assignee: SCHELL GAMES LLC, Pittsburgh, PA (US)

( * ) Notice: Subject to any disclaimer, the term of this patent is extended or adjusted under 35 U.S.C. 154(b) by 376 days.

(21) Appl. No.: 14/609,132

(22) Filed: Jan. 29, 2015

(51) Int. Cl.
*G09B 23/20* (2006.01)
*G01B 11/24* (2006.01)
*G01N 21/25* (2006.01)
*G06T 7/40* (2017.01)
(Continued)

(52) U.S. Cl.
CPC ............. *G09B 23/20* (2013.01); *G01B 11/24* (2013.01); *G01N 21/255* (2013.01); *G06K 9/4652* (2013.01); *G06K 9/48* (2013.01); *G06T 7/408* (2013.01); *G01N 2201/12* (2013.01); *G06T 2207/20116* (2013.01)

(58) Field of Classification Search
CPC ........ G09B 23/26; G09B 23/20; G09B 23/23; G01B 11/24; G01B 11/2408; G01B 11/2509; G01N 21/255; G06K 9/4652; G06K 9/48; G06T 7/408; G06T 2207/20116; G06T 9/20
USPC ........ 434/278; 382/129, 133, 136, 164, 165, 382/190, 199, 203
See application file for complete search history.

(56) References Cited

U.S. PATENT DOCUMENTS

| 3,841,001 A | * | 10/1974 | Nicholson | ............. | G09B 23/26 434/278 |
| 3,939,581 A | * | 2/1976 | Clarke, Jr. | ............. | G09B 23/26 434/278 |

(Continued)

OTHER PUBLICATIONS

Campbell, D. J., Miller, J. D., Bannon, S. J., & Obermaier, L. M. (2011). An Exploration of the Nanoworld with LEGO Bricks. Journal of Chemical Education, 88(5), 602-606. <http://pubs.acs.org/doi/pdf/10.1021/ed100673k>.*

(Continued)

*Primary Examiner* — Sam Yao
*Assistant Examiner* — Michael Humphrey
(74) *Attorney, Agent, or Firm* — K&L Gates LLP

(57) ABSTRACT

A modeling system is provided which comprises a physical atomic modeling system structured for use in conjunction with a computer-implemented application which can execute a vision detection and analysis algorithm. When used to form molecular representations or models, the modeling system can be used to make molecular bonding visible, tangible, and more readily understandable to a student or other user. Various embodiments of the invention leverage the effectiveness of tangible, tactile systems to create a learning experience which increases understanding of atomic bonding at the valence electron interaction level.

18 Claims, 33 Drawing Sheets

(51) Int. Cl.
*G06K 9/46* (2006.01)
*G06K 9/48* (2006.01)

(56) References Cited

U.S. PATENT DOCUMENTS

| | | | | |
|---|---|---|---|---|
| 3,998,003 | A * | 12/1976 | Rosenbaum | A63H 33/102 434/211 |
| 8,126,264 | B2 * | 2/2012 | Kaftory | H04N 1/6033 382/165 |
| 8,280,140 | B2 * | 10/2012 | Levenson | G06K 9/00127 356/36 |
| 8,320,679 | B2 * | 11/2012 | Li | G06K 9/4609 382/152 |
| 8,374,829 | B2 * | 2/2013 | Jakobsen | G06T 17/10 345/8 |
| 2003/0081819 | A1 * | 5/2003 | Connell | G01N 21/253 382/129 |
| 2004/0043164 | A1 * | 3/2004 | Vicentelli | A47F 5/14 428/34.1 |
| 2004/0072137 | A1 * | 4/2004 | Lapa | G09B 5/02 434/386 |
| 2005/0004764 | A1 * | 1/2005 | Sherman | G06F 3/011 702/19 |
| 2006/0099877 | A1 * | 5/2006 | Anderson | G09B 23/26 446/92 |
| 2006/0291713 | A1 * | 12/2006 | Moriya | G01N 21/8851 382/147 |
| 2010/0167819 | A1 * | 7/2010 | Schell | A63F 13/10 463/36 |
| 2011/0170738 | A1 * | 7/2011 | Horovitz | G06K 9/00664 382/100 |
| 2011/0298922 | A1 * | 12/2011 | Horovitz | A63F 13/06 348/143 |
| 2012/0219228 | A1 * | 8/2012 | Osako | G06K 9/3275 382/199 |
| 2013/0154985 | A1 * | 6/2013 | Miyazaki | G06F 3/0418 345/173 |
| 2013/0321447 | A1 * | 12/2013 | Horovitz | A63F 13/06 345/589 |
| 2014/0105456 | A1 * | 4/2014 | Horovitz | G06K 9/00375 382/103 |
| 2014/0206443 | A1 * | 7/2014 | Sharp | G06T 7/0075 463/31 |
| 2014/0370478 | A1 * | 12/2014 | Pfeiffer | G09B 23/24 434/278 |
| 2014/0378023 | A1 * | 12/2014 | Muthyala | G06T 19/00 446/91 |
| 2015/0017624 | A1 * | 1/2015 | Drapela | G09B 23/26 434/278 |
| 2015/0235568 | A1 * | 8/2015 | Hoelzer | G09B 23/26 434/279 |
| 2016/0110873 | A1 * | 4/2016 | Engel | G09B 19/24 382/106 |
| 2016/0189426 | A1 * | 6/2016 | Thomas | G06T 19/006 345/633 |
| 2016/0278599 | A1 * | 9/2016 | Seo | A47L 9/2826 |

OTHER PUBLICATIONS

MRSEC Educational Group, "Lego Molecular-scale Models" University of Wisconsin-Madison, PDF on UWM website, Earliest verifed retrival: Oct. 7, 2014 at http://education.mrsec.wisc.edu/77.htm <http://education.mrsec.wisc.edu/documents/LEGO_Molecular_Scale_Model_Binder.pdf>.*

* cited by examiner

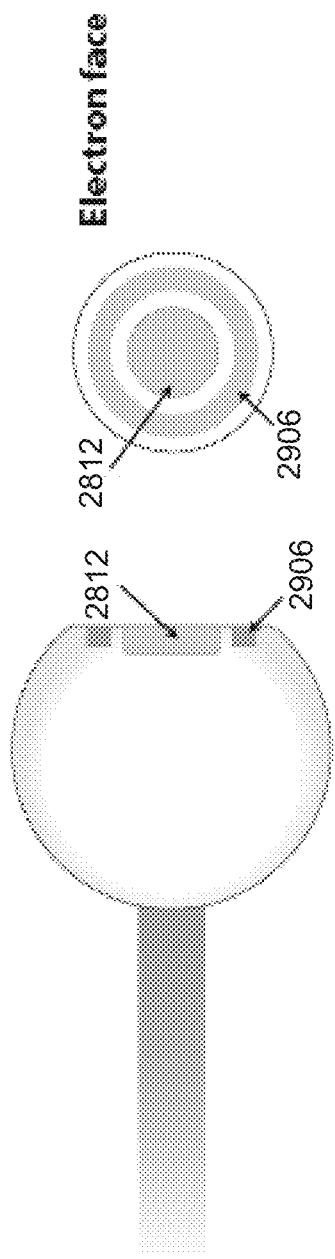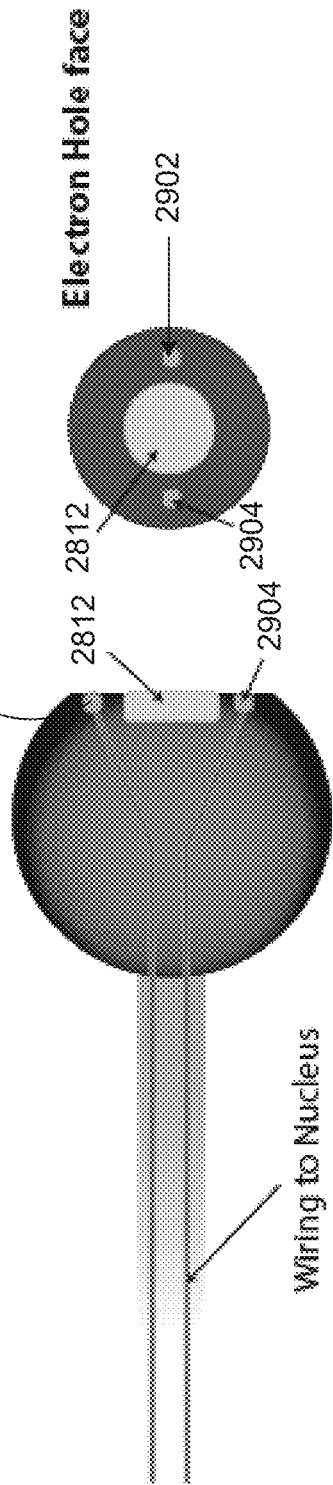

ATOMIC AND MOLECULAR MODELING SYSTEM

FIELD OF THE INVENTION

Various embodiments of the invention generally relate to tools, devices, and techniques for modeling atoms and their chemical bonding behavior when the atoms are combined to form molecular structures. In certain embodiments, the invention more particularly relates to using a physical atomic modeling apparatus in association with execution of computer vision technology for analyzing and identifying different molecular structures formed with various atoms.

BACKGROUND

Learning chemistry can be a daunting task for many students including students at the middle school and high school age levels, for example. Increased engagement in chemistry topics would be beneficial for students who typically struggle with abstract concepts such as atomic bonding and how molecules are formed. Also, heightened exposure, understanding, and exploration of chemistry topics would be useful for educating children even at younger ages. It would be helpful to have tools and techniques for teaching atomic and molecular concepts which can be readily integrated into the existing curriculum of a classroom or home-based environment. An improved approach to teaching these concepts should involve allowing students to learn in a tactile, hands-on manner and helping those with different learning preferences to achieve a better level of comprehension.

In view of these issues, enhanced tools, devices, and techniques are needed for constructing and analyzing physical models which can aid in the instruction of how different elements behave and interact on an atomic and molecular level.

BRIEF DESCRIPTION OF THE FIGURES

The discussion contained in the detailed description is associated with the accompanying figures, in which:

FIGS. 29A and 29B schematically illustrate aspects of an example of a valence electron bonding arm;

FIGS. 30A and 30B schematically illustrate aspects of an example of an electron hole bonding arm;

DETAILED DESCRIPTION

Figure 1:
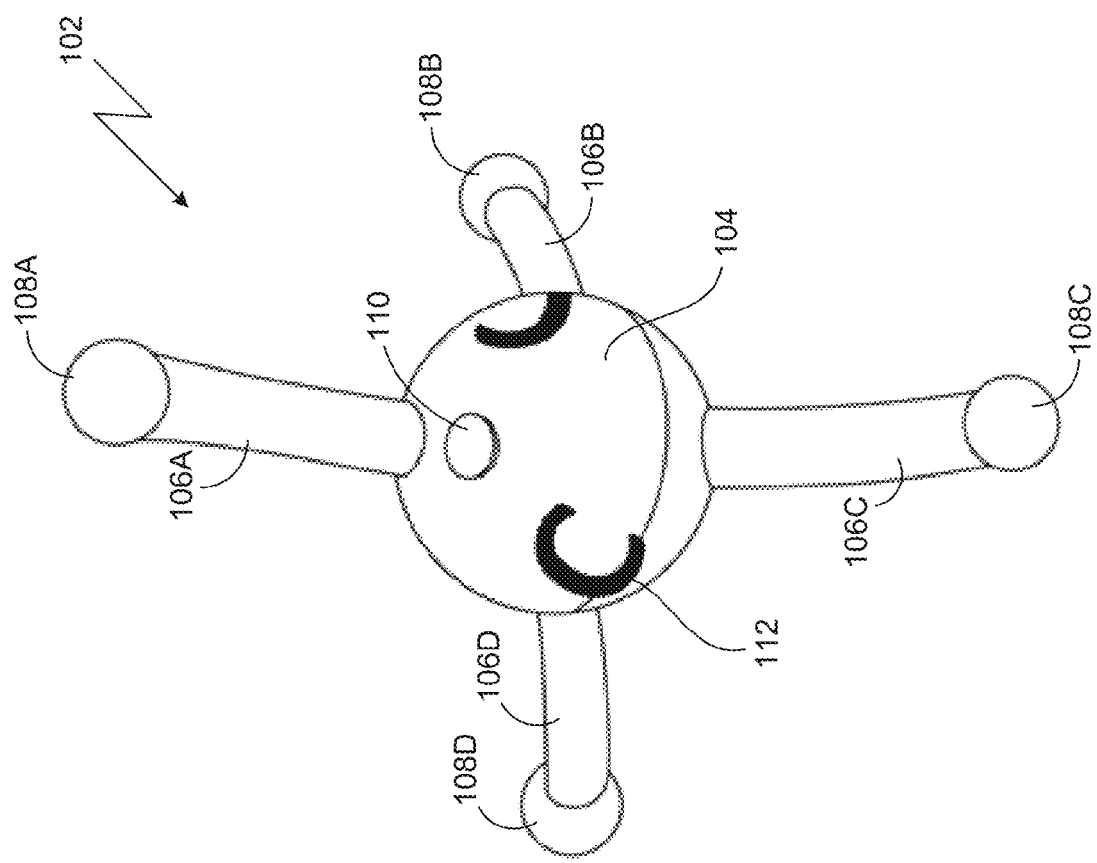
FIGS. 1 and 2 illustrate examples of physical atomic models.

Various embodiments of the present invention may include a modeling system comprising a physical atomic modeling system structured for use in conjunction with a computer-implemented application which can execute a vision detection and analysis algorithm. When used to form molecular representations or models, the modeling system can be used to make molecular bonding visible, tangible, and more readily understandable at the level of electron-nucleus attraction and electron-electron repulsion. Various embodiments of the invention leverage the effectiveness of tangible, tactile systems to create a learning experience which increases the understanding of atomic bonding at the valence electron interaction level. In certain embodiments, the computer-implemented application may be offered with classroom resources for teaching students to explore concepts ranging from basic chemical bonding to balancing chemical equations, for example, in an entertaining and engaging manner.

In certain embodiments, the atomic modeling system may comprise a set of atomic representations or atomic models that can be connected together physically (e.g., by magnets or other similar mechanical means) to form representations of various molecular structures or molecular models. Each of the atomic models may be structured to include a specific configuration of structures representing valence electrons, structures representing chemical bonds between atoms, and one or more physical bonding sites for facilitating connections with one or more other atoms to construct a molecular model.

To recreate the atomic structure of an element, the atomic models may be structured with a colored plastic nucleus, for example, with a number of magnetic valence electrons extending from the nucleus in the form of one or more silicone arms, for example. The surface of each model nucleus may have one or more magnetic bonding sites with which the "electron" portions of other atom models can connect to form a molecular model. In certain embodiments, the modeling system can provide representations or models of both covalent and ionic bonding, as well as double and triple bonding. For example, models of elements that tend to lend their electrons may not have bonding sites on their nuclei, as such elements tend not to accept electrons when bonded ionically.

In various embodiments, an interactive computer-implemented application can be provided which uses a computer vision system and an operatively associated vision detection and analysis algorithm to recognize atomic models or molecular models built by students or other users. The application can be configured to compare a constructed model against a database (or other data storage medium) of molecules or compounds. When the application recognizes a molecule, information can be presented to the user about the molecule, its properties, and how it is used in everyday life, for example. The molecule may then be stored in a collection for later reference. Alternatively, the application can be programmed to communicate to the user that a particularly constructed molecule does not match an entry in the database, perhaps indicating that the user has not constructed a molecule correctly.

In certain embodiments, a set of atomic models may include various model atoms selected from the periodic table, including for example and without limitation: hydrogen, lithium, beryllium, carbon, nitrogen, oxygen, fluorine, sodium, magnesium, phosphorus, sulfur, and chlorine. Functionally, each atomic model may be configured to be identifiable by size, color, and/or by a number of magnetically attractive portions (e.g., valence electrons) suspended around its nucleus structure by one or more of its bonding arms.

FIG. 1 illustrates an example of an atomic model 102 which can be configured in accordance with various embodiments of the invention. In the example shown, the atomic model 102 represents a carbon atom having four valence electrons in its outer shell. The model 102 includes a nucleus structure 104 with four bonding arms 106A-106D extending from the nucleus structure 104. At the distal end of each arm 106A-106D a magnetically attractive portion 108A-108D is positioned which is comprised of metal or another suitable material structured for magnetic attraction to one or more bonding sites of another atomic model, for example. In conjunction with the bonding arms 106A-106D, each magnetically attractive portion 108A-108D represents a valence electron of the atom in the model 102. The model 102 includes one or more of its own bonding sites 110 comprised of a magnetic material for attracting (or repulsing) a magnetically attractive portion attached to the bonding arm of another atomic model, for example. In certain embodiments, the atomic model 102 may be marked with one or more indicia 112 which indicate the type of atom represented by the atomic model 102 (e.g., the letter "C" to indicate a carbon atom).

Figure 2:
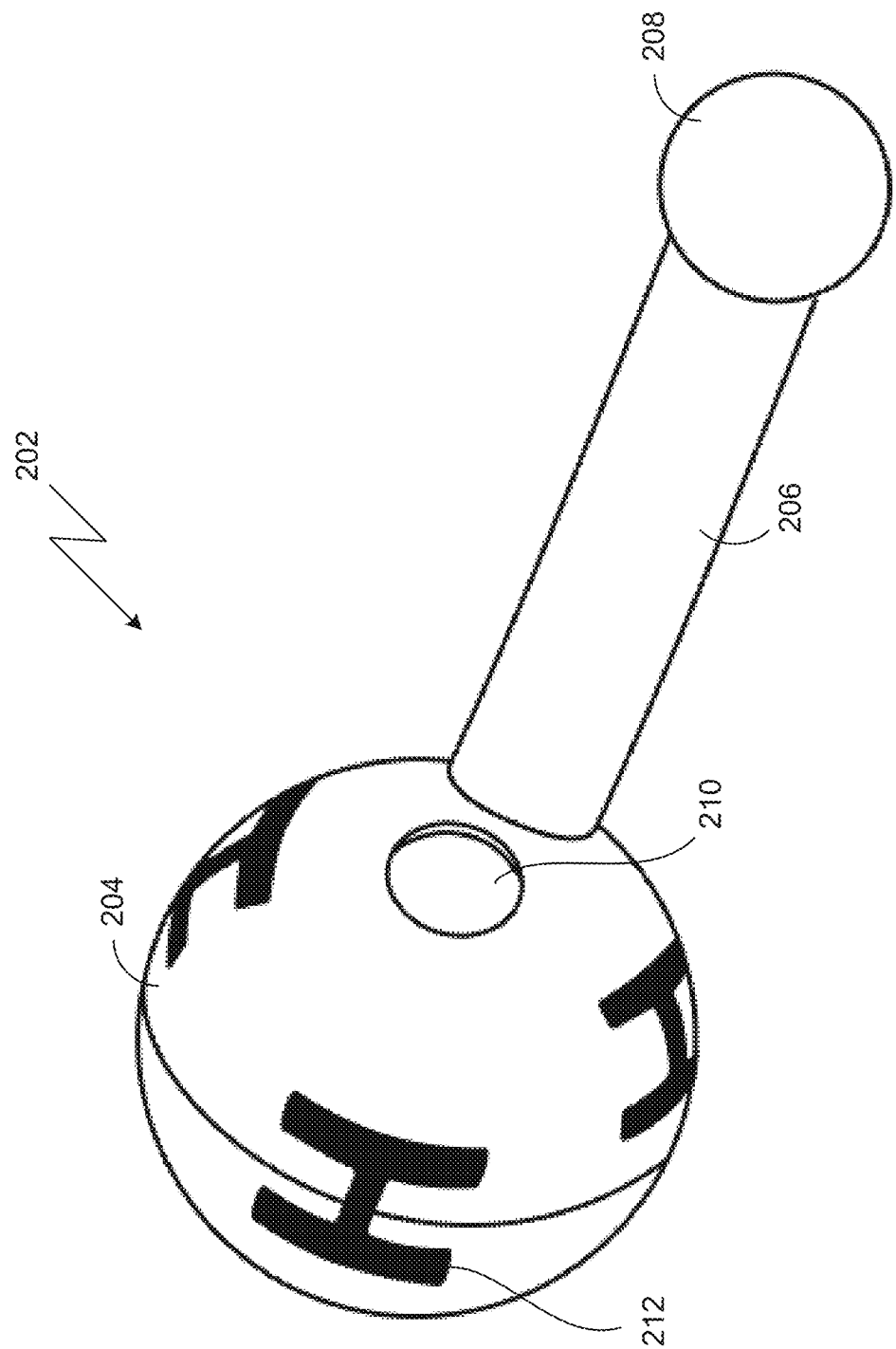

FIG. 2 illustrates another example of an atomic model 202 which may be connected to the atomic model 102, for example, to form one or more kinds of molecular structures. The model 202 may include a nucleus structure 204 with a bonding arm 206 extending from the nucleus structure 204. At the distal end of the arm 206 a magnetically attractive portion 208 is positioned which is comprised of metal or another suitable material structured for magnetic attraction to one or more bonding sites of another atomic model, for example. In conjunction with the bonding arm 206, the magnetically attractive portion 208 represents a valence electron of the atom in the model 202. The model 202 includes one or more of its own bonding sites 210 comprised of a magnetic material for attracting (or repulsing) a magnetically attractive portion attached to the bonding arm of another atomic model, for example. In certain embodiments, the atomic model 202 may be marked with one or more indicia 212 which indicate the type of atom represented by the atomic model 202 (e.g., the letter "H" to indicate a hydrogen atom).

Figure 3:
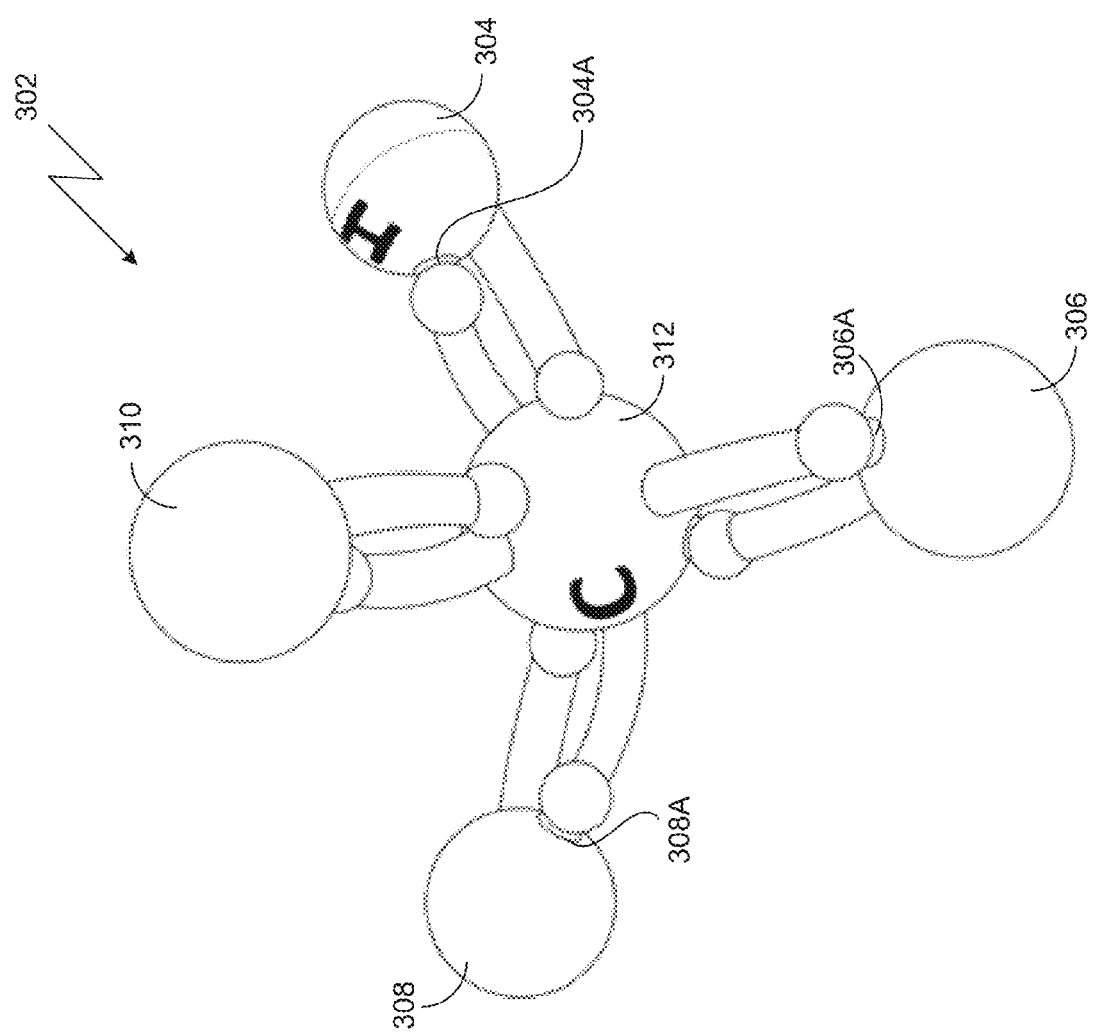
FIG. 3 illustrates an example of a molecular model.

FIG. 3 illustrates an example of a molecular model 302 which can be formed by attaching together multiple atomic models 304, 306, 308, 310, 312. In this example, four hydrogen atomic models 304, 306, 308, 310 are connected to a carbon atomic model 312 to form the molecular model 302. As described above, the various atomic models 304, 306, 308, 310, 312 may be connected magnetically at the various bonding sites of each atomic model, such as bonding sites 304A, 306A, 308A, for example, to form the molecular model 302 for a methane molecule, as shown.

Figure 4:
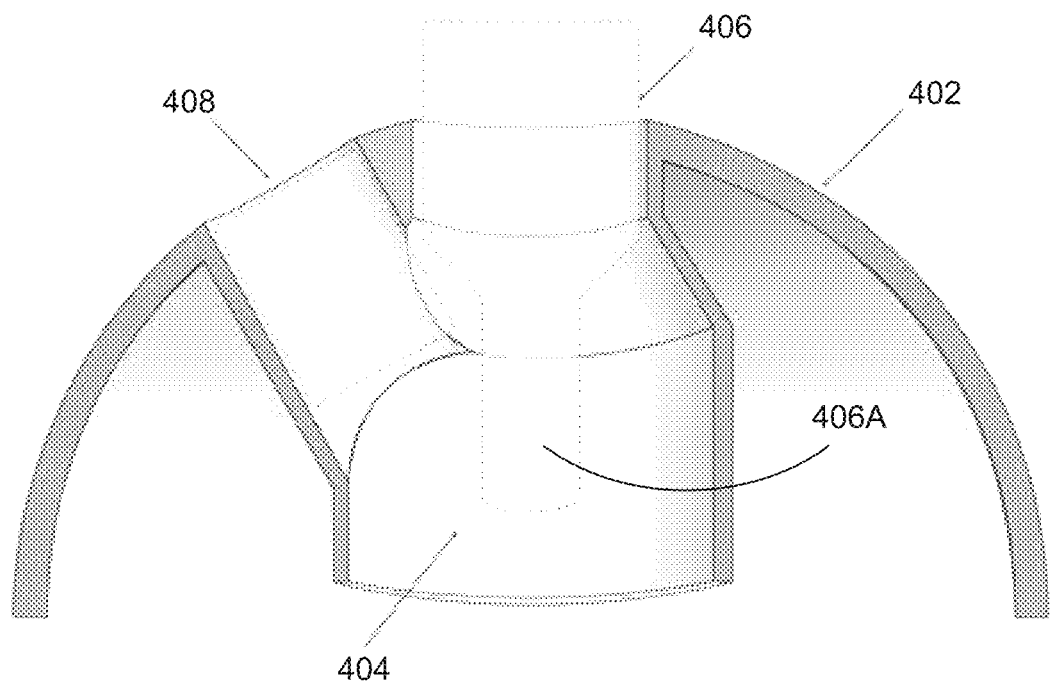
FIG. 4 illustrates an example of a portion of an interior of a nucleus structure of an atomic model.
Figure 5:
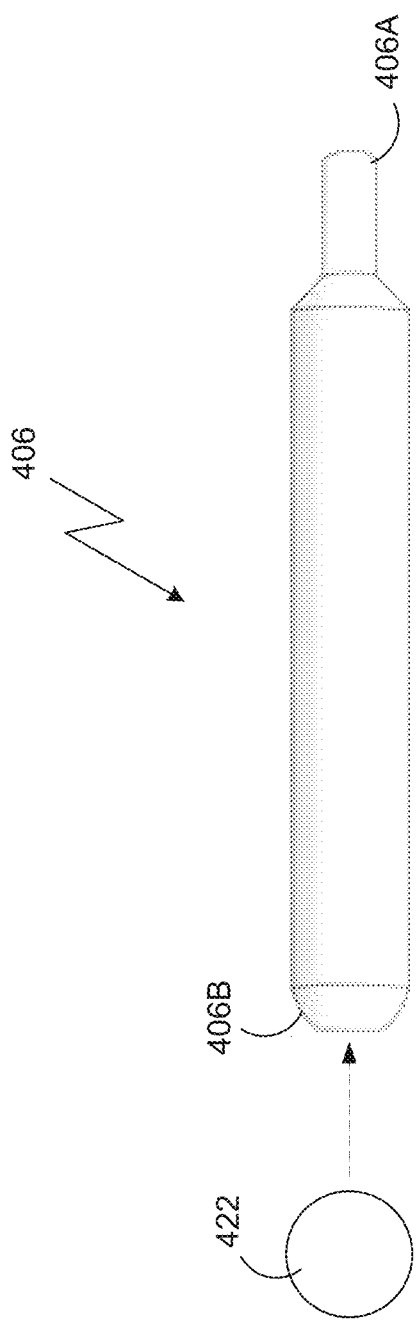
FIG. 5 illustrates an example of a bonding arm structured for use with an atomic model.

FIG. 4 illustrates an example of a portion of an interior of a nucleus structure 402 of an atomic model structured in accordance with certain embodiments of the invention. In this example, the nucleus structure 402 includes an interior attachment area 404 configured to receive a bonding arm 406 and a magnet 408 therein. The magnet 408 may be provided for a bonding site of the nucleus structure 402. FIG. 5 illustrates an example of the bonding arm 406, including a proximate end 406A structured for insertion into the interior attachment area 404 of the nucleus structure 402, and a distal end 406B structured to secure a magnetically attractive portion 422 thereon representing an electron of the atom.

In various embodiments, the bonding arm 406 may be comprised of silicone (e.g., Smooth-On Dragon-Skin 37 or Durometer 37) or another suitably structurally similar material that provides both sufficient stiffness and flexibility for the embodiments described herein. The magnet 408 may be comprised of a 0.25" diameter×0.5" length n52 cylinder magnet, for example, or various sizes and brands of neodymium or ceramic magnets. The magnetically attractive portion 422 may be comprised of a modified ⅜%" silver jingle bell, for example. The body of the nucleus structure 402 may be a three-dimensional printed sphere printed on a Vanguard SI$^2$ HS SLS system using Duraform PA powder, for example, or by using ABS plastic on a Makerbot Replicator II. The interior attachment area 404 may be filled with silicone, for example, or another suitable material to secure the bonding arm 406 and the magnet 408 in place within the nucleus structure 402.

In certain embodiments, the nucleus of an atomic model may be provided in a variety of different colors, such as by using a CPK color scheme or other color palettes, to indicate a type of atom represented by the atomic model. Indicia displayed on the nucleus of an atomic model may be complementarily colored, contrastingly colored, or colored differently than the nucleus to highlight the type of atom, for example. Different nuclei sizes may be employed to reflect the type of atom and/or its importance in the construction of molecular models. For example, hydrogen nuclei may be provided as smaller in size compared to other atoms to reflect their prevalence or importance in the modeling process. In certain embodiments, variations of the weight of nuclei may be implemented depending on the atomic weight of the atom represented by an atomic model. In other aspects, size differences for the nucleus of an atomic model can be implemented to differentiate between atomic sizes based on the periods (rows) of the periodic table. This can simulate the size difference of atoms represented by the organization of the periodic table itself. For example, four different nucleus sizes may be used to represent the four periods of elements.

Figure 6A:
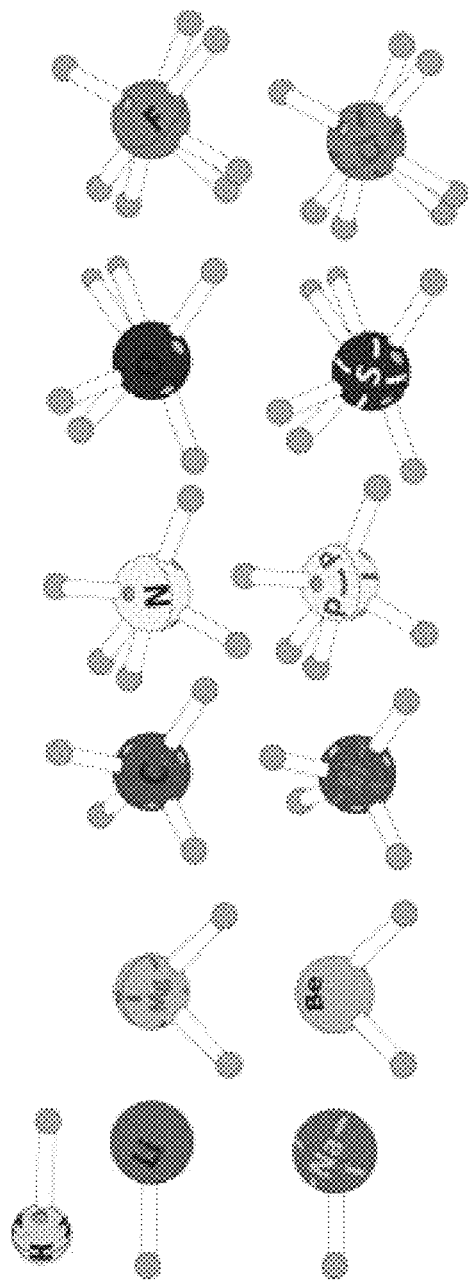
FIGS. 6A and 6B illustrate various examples of atomic models.
Figure 6B:
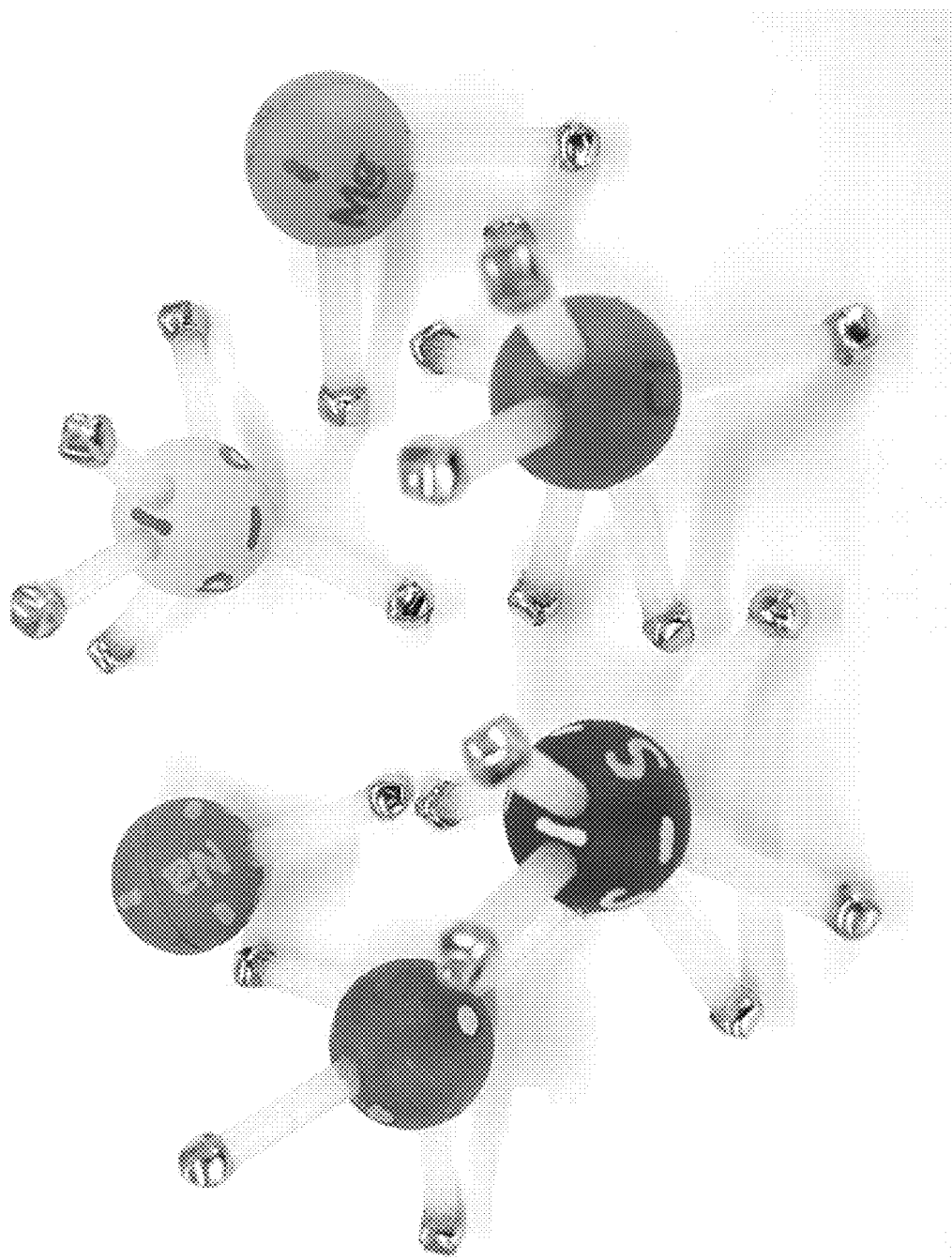

In other aspects, different bonding angles may be employed for the bonding arms with respect to the connection to the nucleus of an atomic model. In certain embodiments, one or more bonding sites of an atomic model may be highlighted with either a bright color, a frown face, or other indicia to make the bonding sites more visually perceptible by a user. FIGS. 6A and 6B illustrate various examples of atomic models which can be structured in accordance with different embodiments of the invention.

In various embodiments, in order for different elements from the same group to be differentiated by the vision detection and analysis algorithm, a contrasting color symbol can be stenciled or applied onto the nucleus of the atomic model. In this manner, two elements from the same group appear to be visually different to both the student and the algorithm. Elements from the first and second period may use black symbols, for example, and elements from the third period may use a contrasting color glyph or indicia. For example, oxygen (in the second period) may have a dark-blue nucleus with a black symbol, and silicone (in the third period) may have the same dark-blue nucleus with a bright yellow symbol.

In one example of using the atomic models, to simulate covalent bonding, a student connects the metal electron on the tip of a bonding arm of a first atomic model to the magnetic bonding site on the nucleus structure of another atomic model. In the example above, carbon and hydrogen form a covalent bond by lending each other one of their electrons. Hydrogen is satisfied with two electrons in its valence shell, while all other atoms follow the octet rule (i.e., wanting eight electrons in their valence shell). A student is able to observe this by counting the exposed bonding sites on each model. The hydrogen atom's single bonding site is filled by the carbon, which has multiple exposed bonding sites. In an ionic bond, elements that are more willing to give than take an electron have no bonding sites, allowing these elements to donate their electron to another atom. To simulate ionic bonding, a student connects the metal electron of the atom becoming an ion to the bonding site of the atom accepting the electron.

Figure 7:
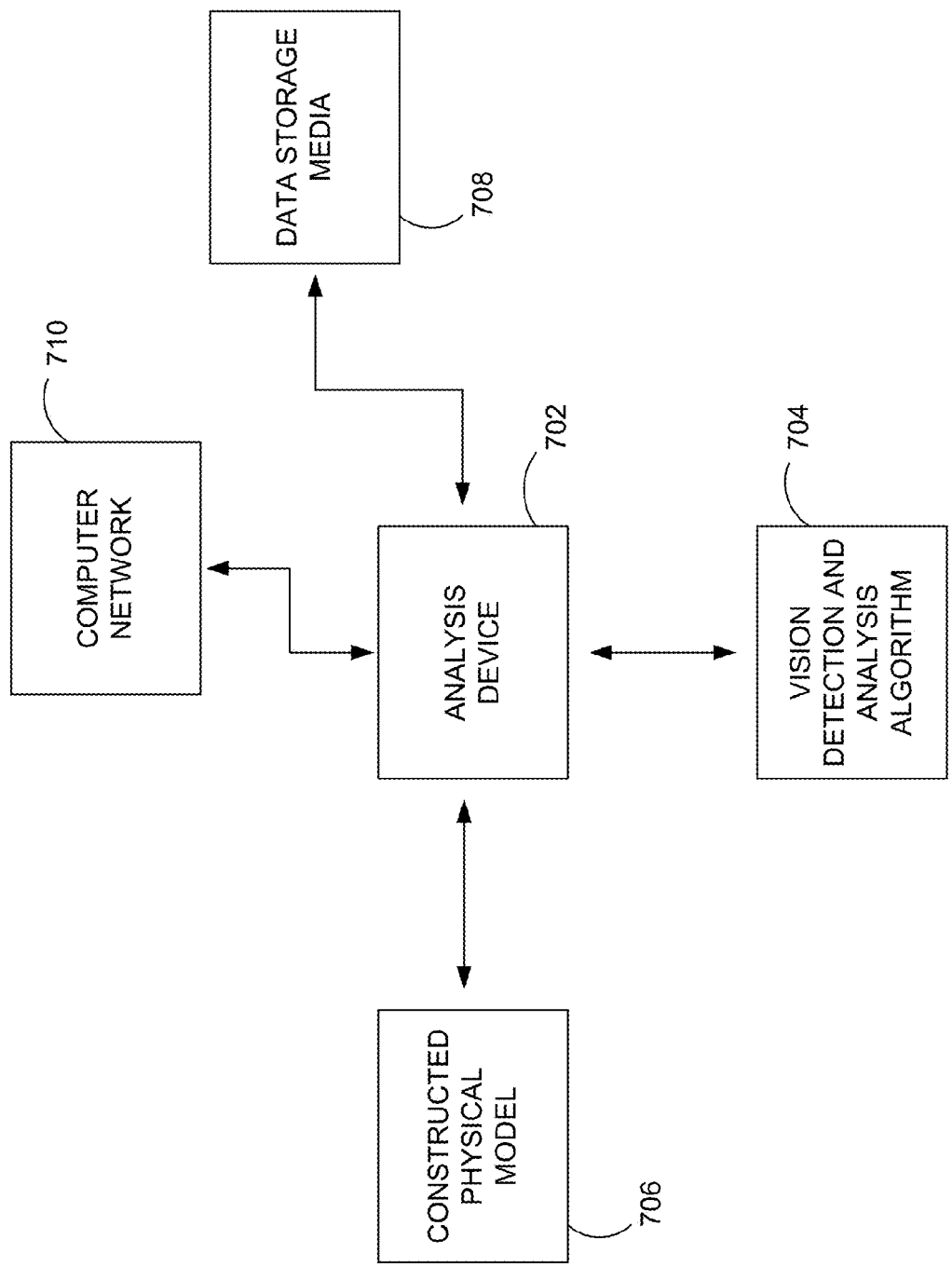
FIG. 7 includes a system architecture diagram including an example of an analysis device programmed for executing a vision detection and analysis algorithm.
Figure 8:
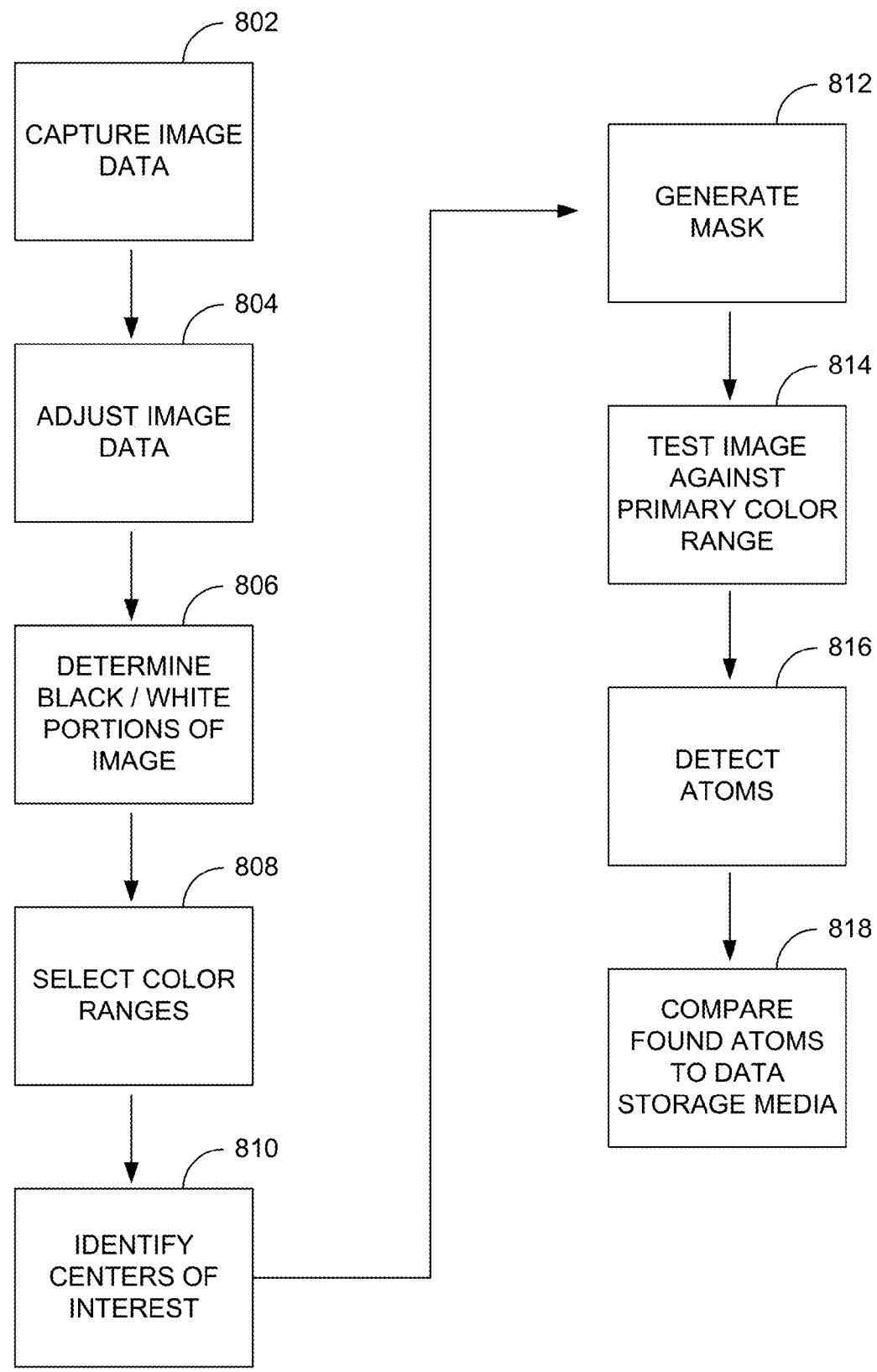
FIG. 8 includes a process flow diagram illustrating examples of the processing of a vision detection and analysis algorithm.

With reference to FIGS. 7 and 8, a computer-based analysis device 702 can be employed to operate an application which can execute a vision detection and analysis algorithm 704 on a constructed physical atomic or molecular model 706 to determine the characteristics of the model 706. The application may be operatively associated with one or more data storage media 708 which contain data about atoms, molecules, atomic models, molecular models, or other related information. The analysis device 702 may be any camera-enabled computing device capable of capturing image data associated with an atomic model or a molecular model. Examples of suitable analysis devices 702 include "iPad" devices, smart phones, digital cameras, or other devices capable of capturing image data associated with an atomic model or a molecular model. The application can be a mobile iOS-based application designed for the iPad family of tablets, for example. The application contains functionality to capture digital images of atomic and molecular models, identify each atom or molecule based on vision recognition, and/or provide information about the identified atom or molecule to user. The vision recognition software can be applied to the image data of the physical model to transform the image into a three-dimensional representation of the constructed molecule. The analysis device 702 may also be configured to communicate data with one or more computing networks 710, such as through an Internet connection.

Figure 9:
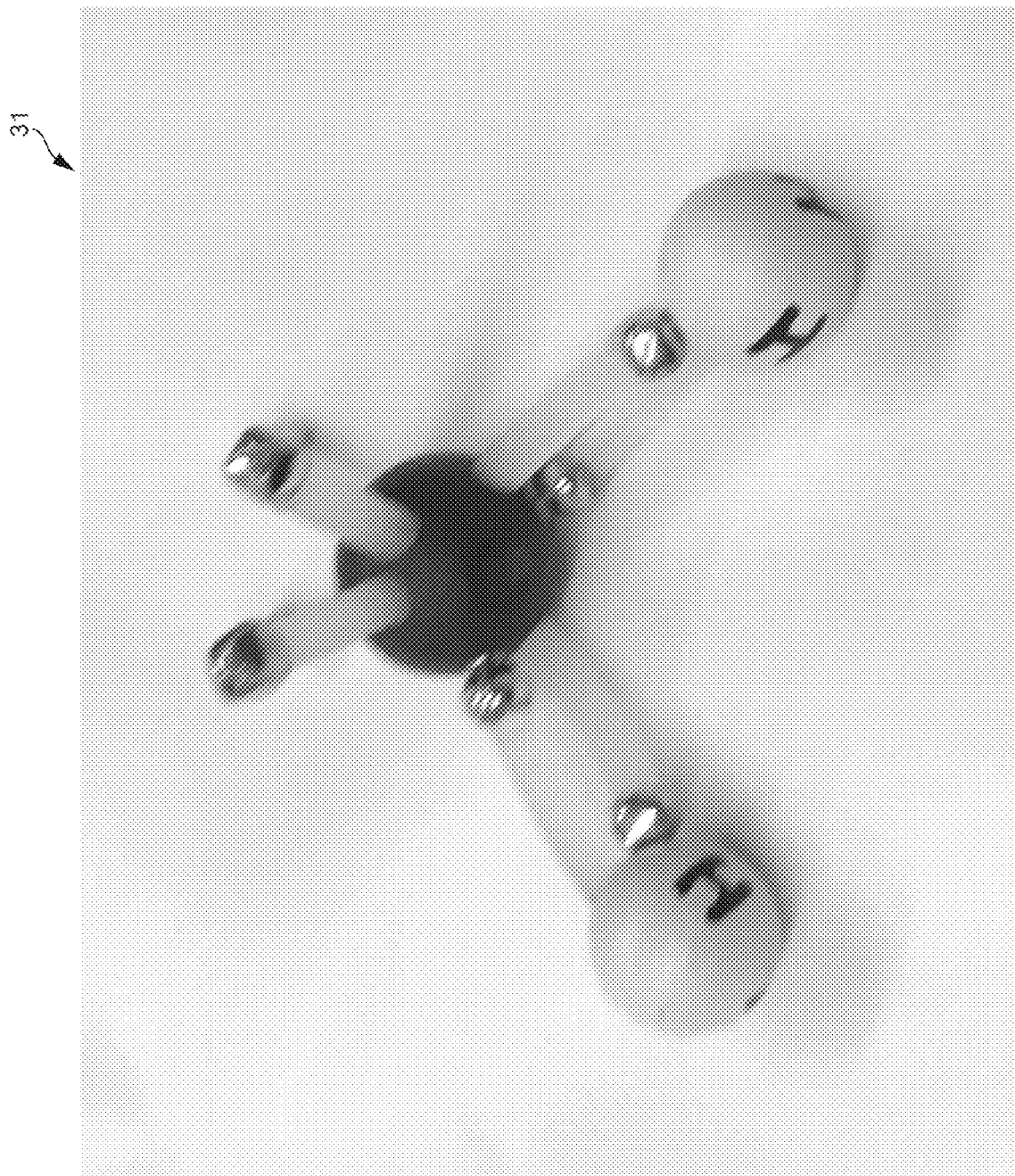
FIGS. 9 through 18 illustrate various aspects of an example of the processing activity which can be performed by one example of a vision detection and analysis algorithm.

With reference to FIG. 8, at action 802 the algorithm 704 may include receiving input data by capturing image data associated with an atomic model or a molecular model, for example. The image may be captured using a built-in camera function of the analysis device 702. A screen of the analysis device 702 may be provided with a guide for framing the model for image capture. FIG. 9 illustrates an example of a base test image 31 of a molecular model captured by the analysis device 702.

Figure 10:
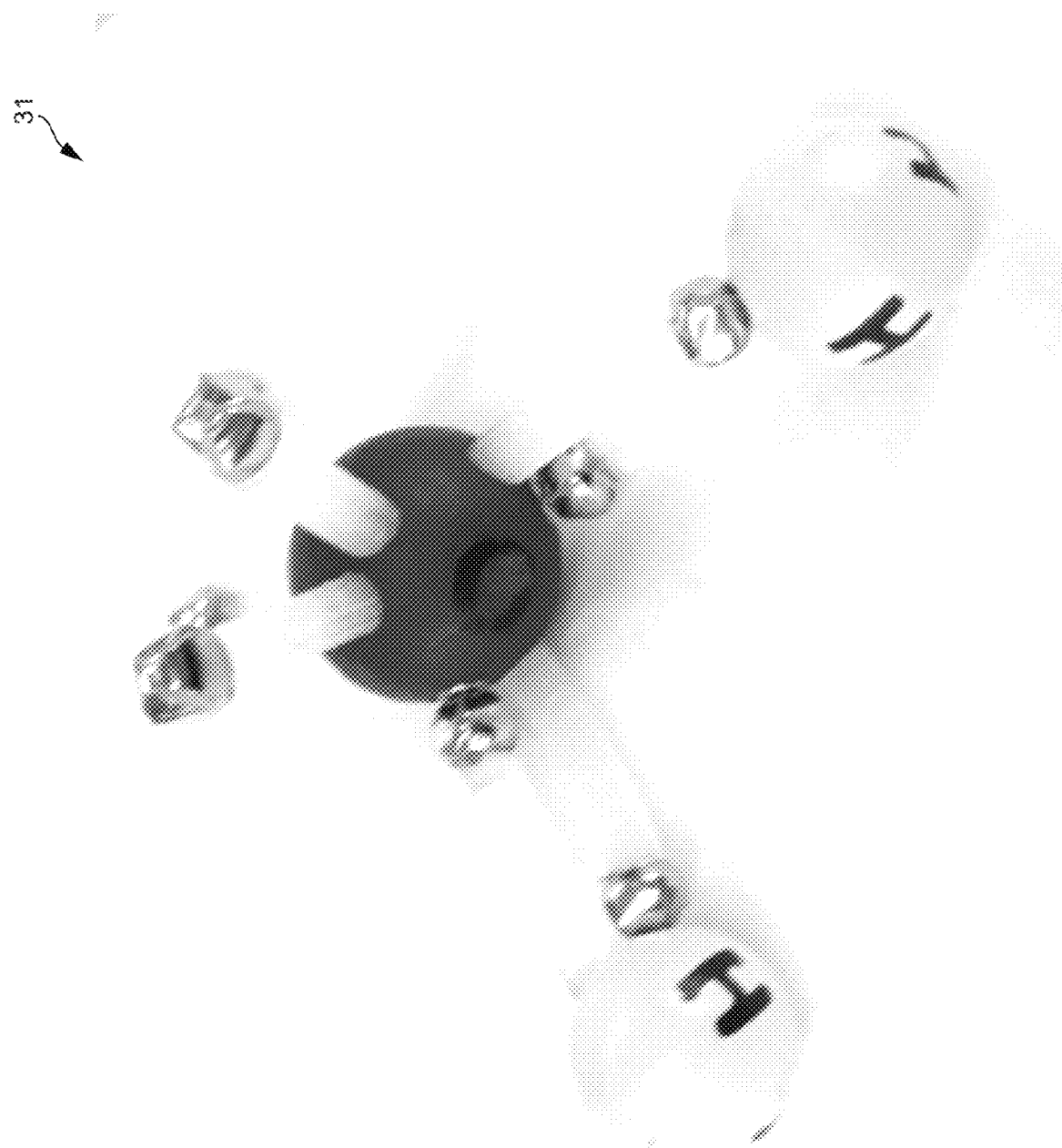

At action 804, the base test image data may be adjusted for color, lighting, resolution, and/or other image characteristics to promote enhanced function of the algorithm 704. This may include retrieving default image data from the camera, adjusting the image characteristics, and/or normalizing the image data based on camera values, for example. FIG. 10 illustrates an example of an image 31 adjusted for color and lighting in accordance with action 804. In various embodiments, a color swatch or color chart may be employed to calibrate the analysis device 702 prior to use. Such calibration may involve accounting for the ambient conditions in which the device 702 is to be employed, such as the lighting within a classroom, for example. In certain embodiments, the color swatch or color chart may be used before or during the image capture processing which is performed by the analysis device 702.

At action 806, an initial test can be performed for finding significant black versus white areas of the captured image. A ratio can be calculated to determine if the image is "light" or "dark" by determining areas of white to black. In this regard, white and black can be considered unique colors, and the algorithm 704 can be configured to look for significant black versus white images. The algorithm 704 may employ one or more "OpenCV" computer vision software functions, for example, to determine whether certain colors are present in different pixels within the image data. It can be seen that this helps with making adjustments for color identification.

Figure 11:
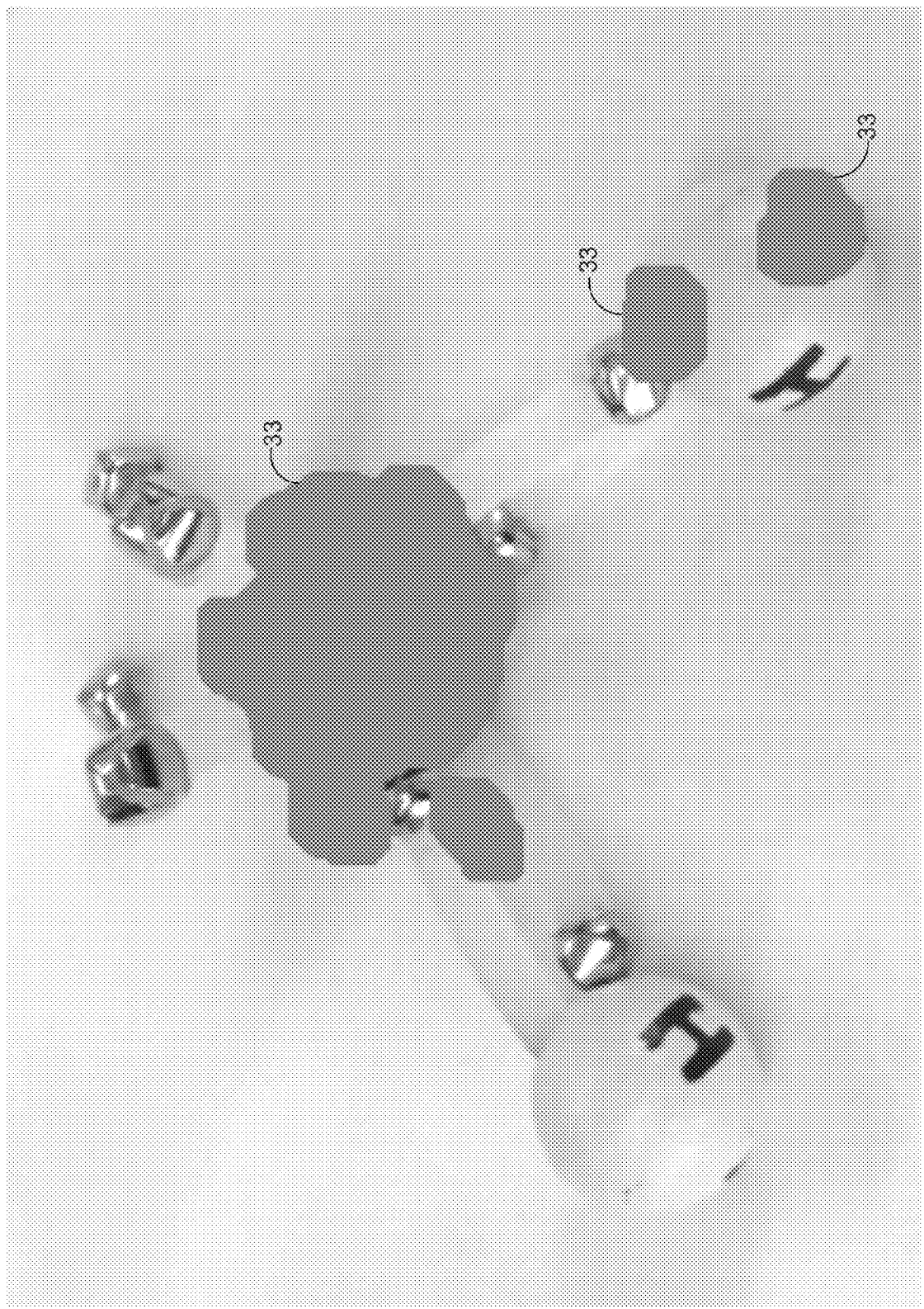

Based on this initial determination, at action 808 a set of specific color ranges can be chosen which are mapped to the primary detection colors used. In this example, the colors pink, light blue, orange, red, yellow, dark blue, green, and purple have been used. At action 810, an image test can be used to determine significant non-black and non-white areas that are likely to be mapped to an atomic structure in the image. These centers of interest can be used at a later stage in the processing performed by the algorithm 704. FIG. 11 illustrates an example of identification of centers of interest 33 including mapping based on atom color and value.

Figure 12:
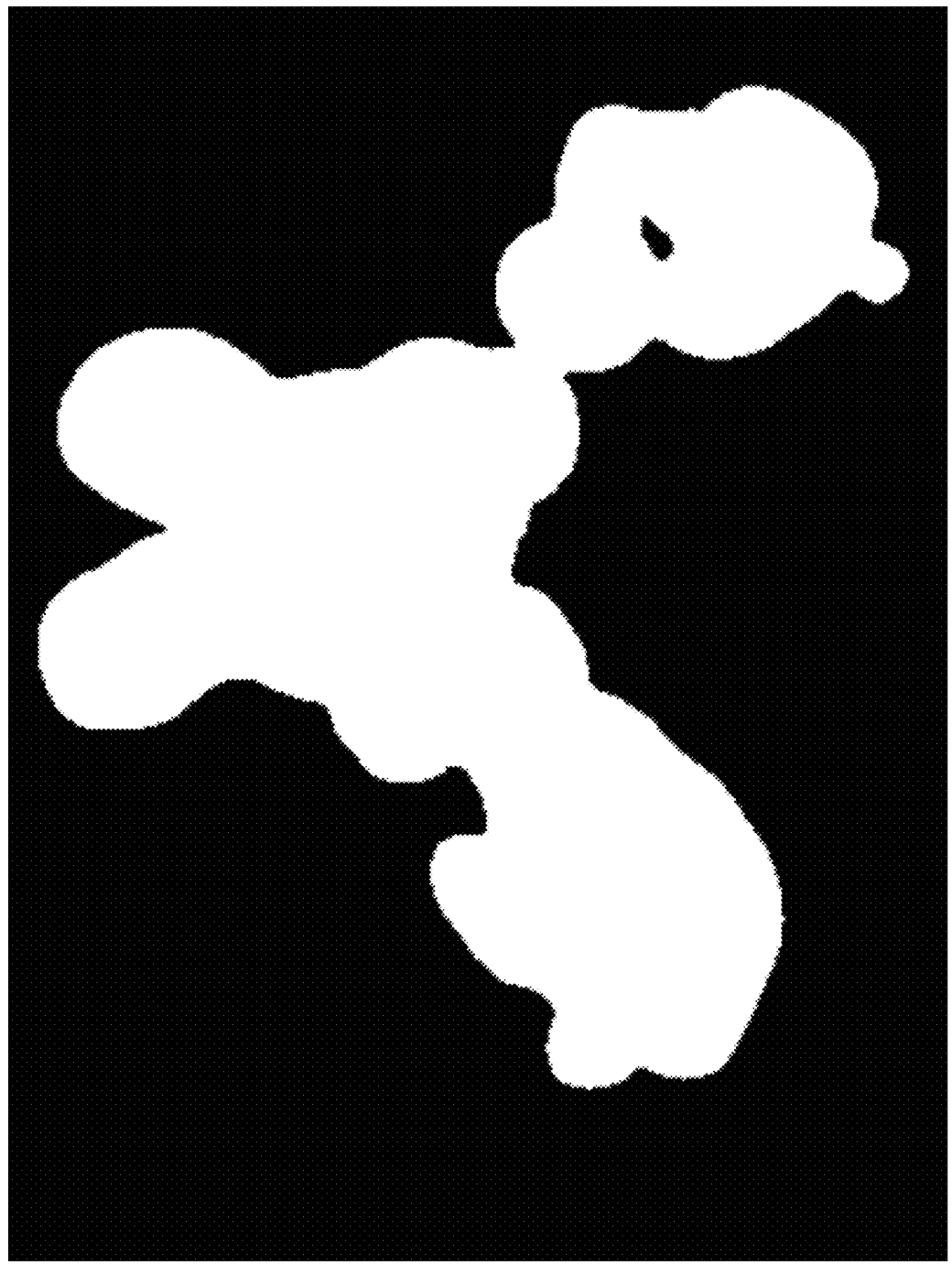

At action 812, another image test can be executed to identify areas to ignore in the image using both the found black/white areas and a fill technique around the edges of the image. This mask can be used throughout the processing of the vision recognition algorithm 704 to avoid unnecessary detection in areas unlikely to have an atom. FIG. 12 includes an example of a generated mask 35 of non-useful areas identified in the test image. At action 814, the image is tested against each primary color range for total area and significant regions found. Each color can be sorted from largest found area to smallest found area, for example, with accompanying color ranges and without any significant found areas discarded.

Figure 13:
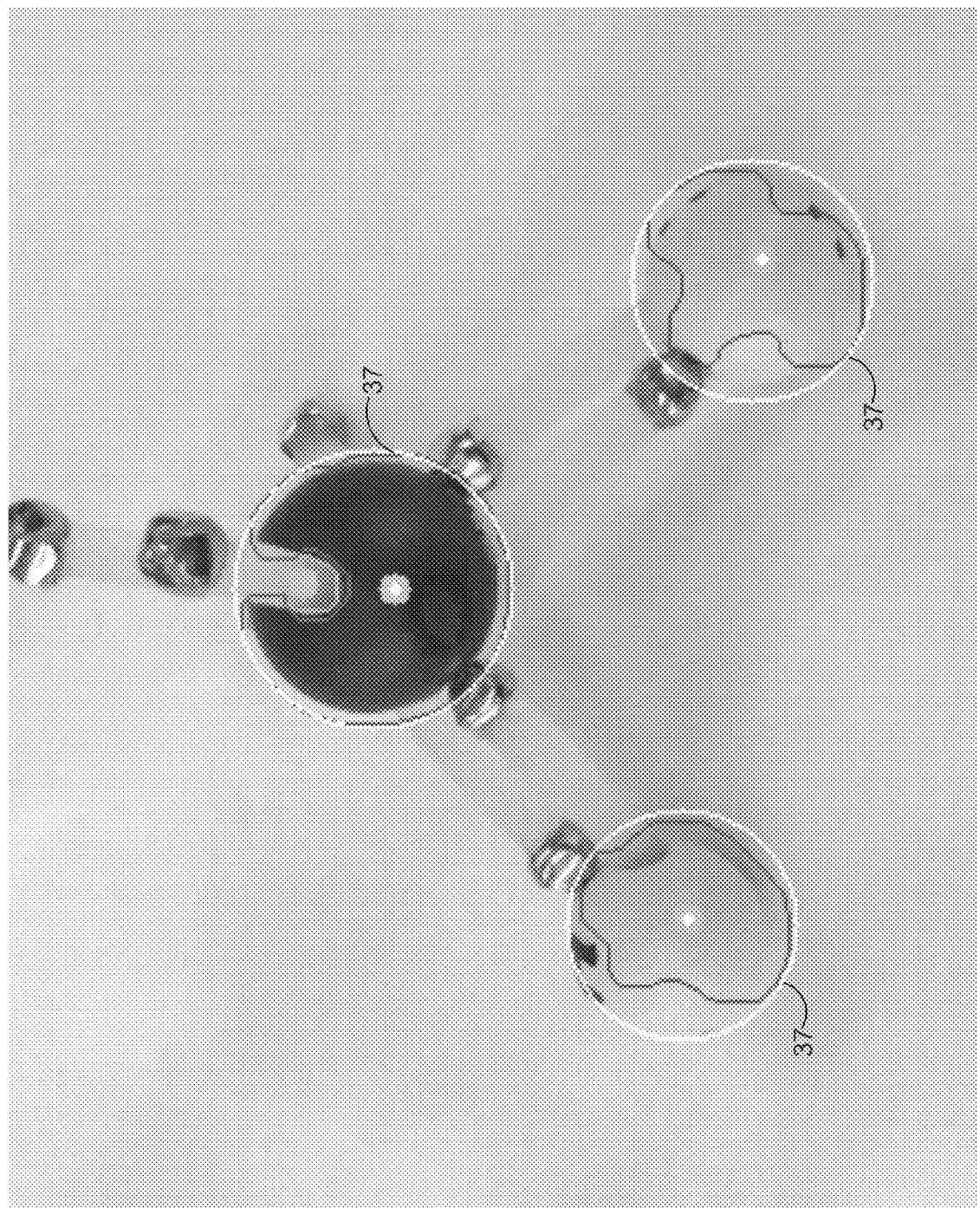
Figure 14:
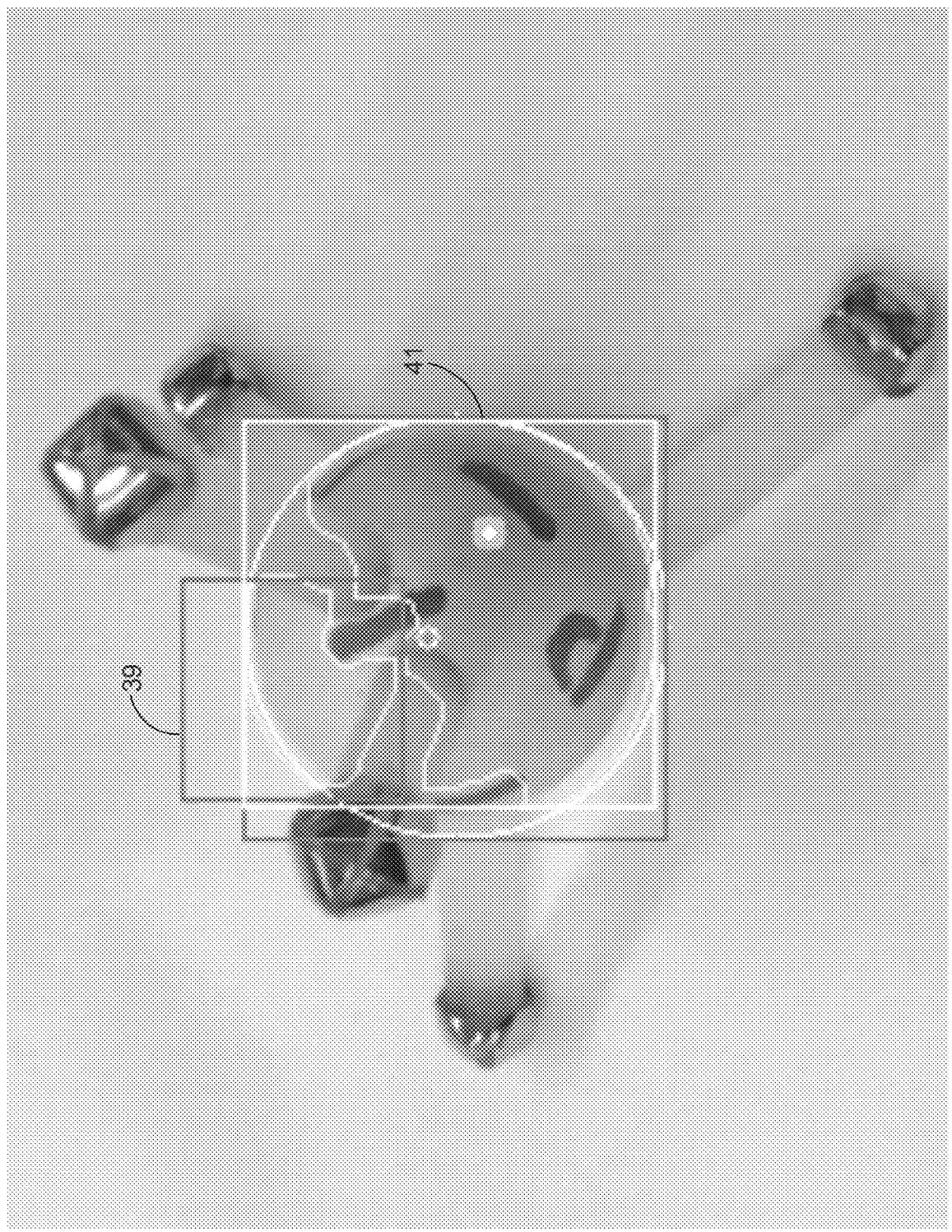
Figure 15:
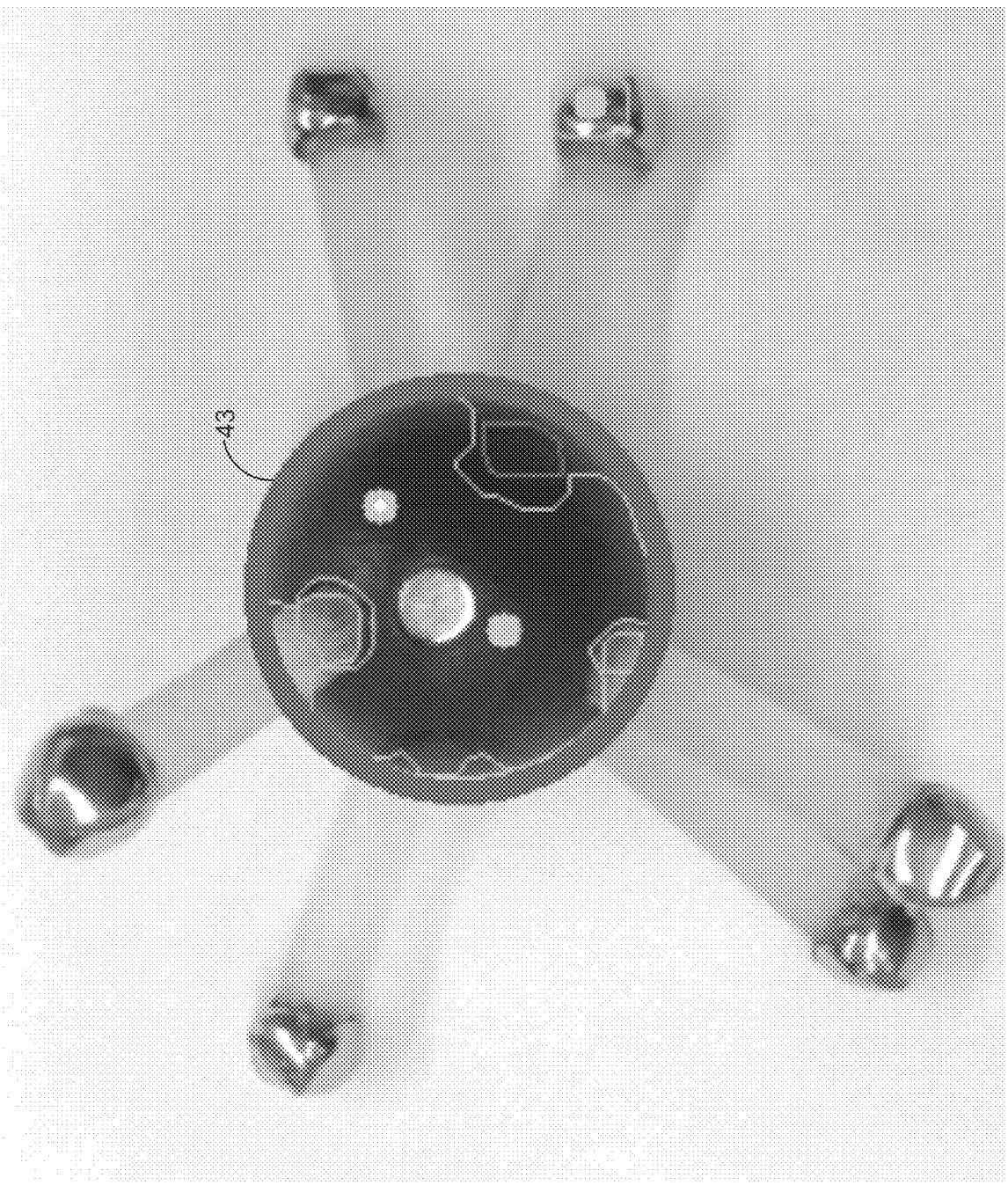

At action 816, the remaining color areas may then be searched and analyzed for individual atom detection. Each found color range has a search executed on the filtered and masked image to identify unique contours within that color range. These contours may be first identified as either significant or non-significant contours with the significant contour centers recorded in a data storage medium 708. FIG. 13 illustrates an example of finding first significant contours 37 within the image. The contours found in this range may then be sorted by size and shape. Each contour may be executed through a best circle fit algorithm. Using predetermined criteria, a sufficient circle fit is given an initial guess of being an atom and the contour is removed from further testing. If this initial test fails on a contour, the contour is then paired against other contours within a specific possible overlapping distance of that contour. Two or more contours may be combined and tested together as a circle fit. This test if successful places these contours as another guess as an atom, and these guesses can be removed from further testing. An example of combining separate contours 39, 41 in this manner is illustrated in FIG. 14.

If the combined contour test fails, then the algorithm 704 may be configured to attempt to combine the contour with other contours from like-colored color ranges that may exist (like colors being colors that may occur in pair with each other such as blue-purple, yellow-green, pink-red, red-orange). These contours can be combined together and tested using the circle fit test again. A successful test places these contours as another guess as an atom, and the guesses are removed from further testing.

At action 816, the remaining color areas may then be searched and analyzed for individual atom detection. Each found color range has a search executed on the filtered and masked image to identify unique contours within that color range. These contours may be first identified as either significant or non-significant contours with the significant contour centers recorded in a data storage medium 708. FIG. 13 illustrates an example of finding first significant contours 37 within the image. The contours found in this range may then be sorted by size and shape. Each contour may be executed through a best circle fit algorithm. Using predetermined criteria, a sufficient circle fit is given an initial guess of being an atom and the contour is removed from further testing. If this initial test fails on a contour, the contour is then paired against other contours within a specific possible overlapping distance of that contour. Two or more contours may be combined and tested together as a circle fit. This test if successful places these contours as another guess as an atom, and these guesses can be removed from further testing. An example of combining separate contours 39, 41 in this manner is illustrated in FIG. 14.

Figure 16:
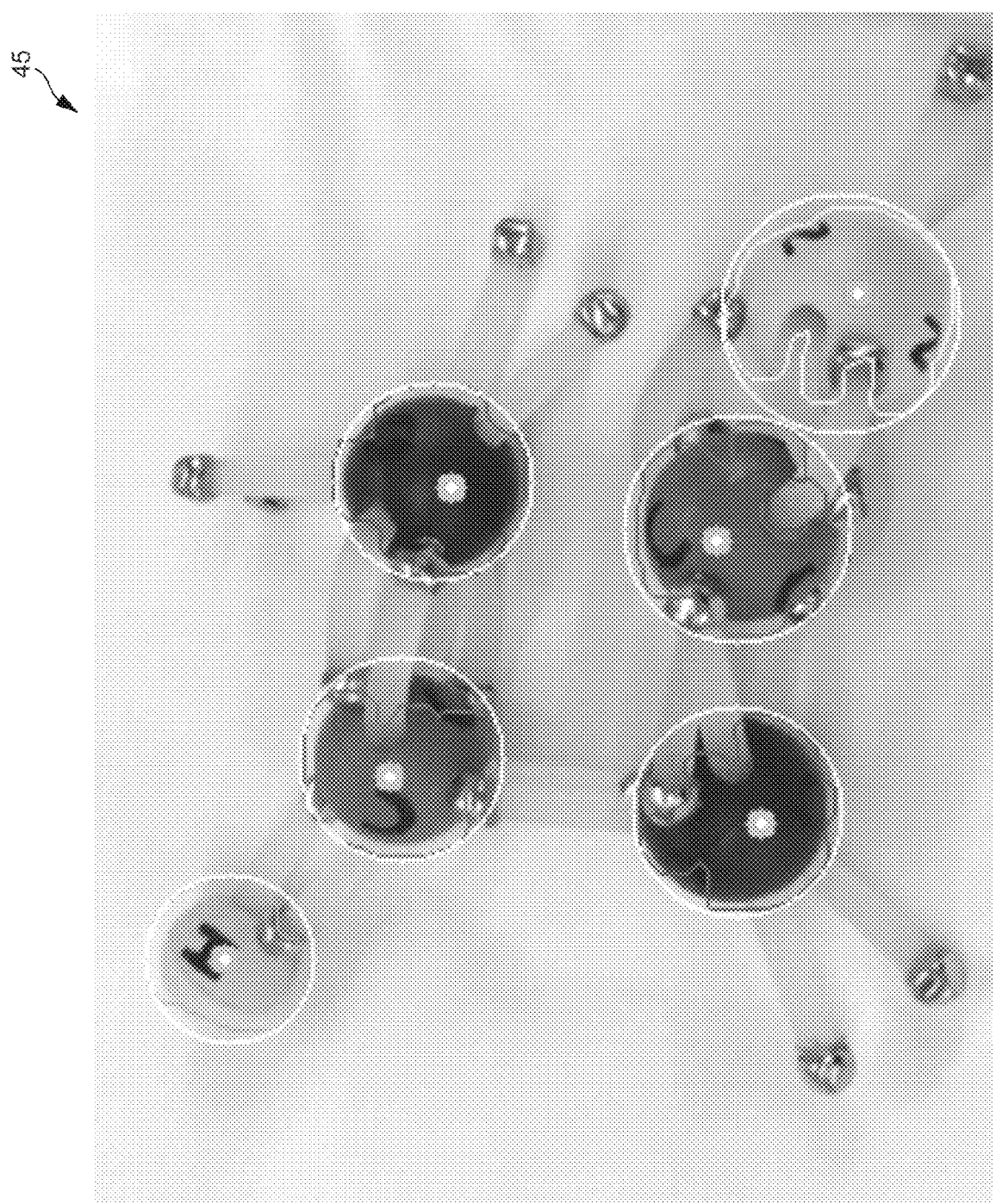

After the contour tests have been completed, the found atoms and contours may be processed through one or more best estimate size tests. If there is no initial best guess size, then these atoms can be used as a benchmark for future atom size testing. If a best guess size has been found, then the found atoms can be compared against these sizes and accepted or rejected within a specific margin or predetermined range. One or more additional tests may be run at this point to determine if rejected contours can be accepted if split or merged with other contours in the test. FIG. 16 illustrates an example of the test image 45 after color and contour shape tests have been executed.

Figure 17:
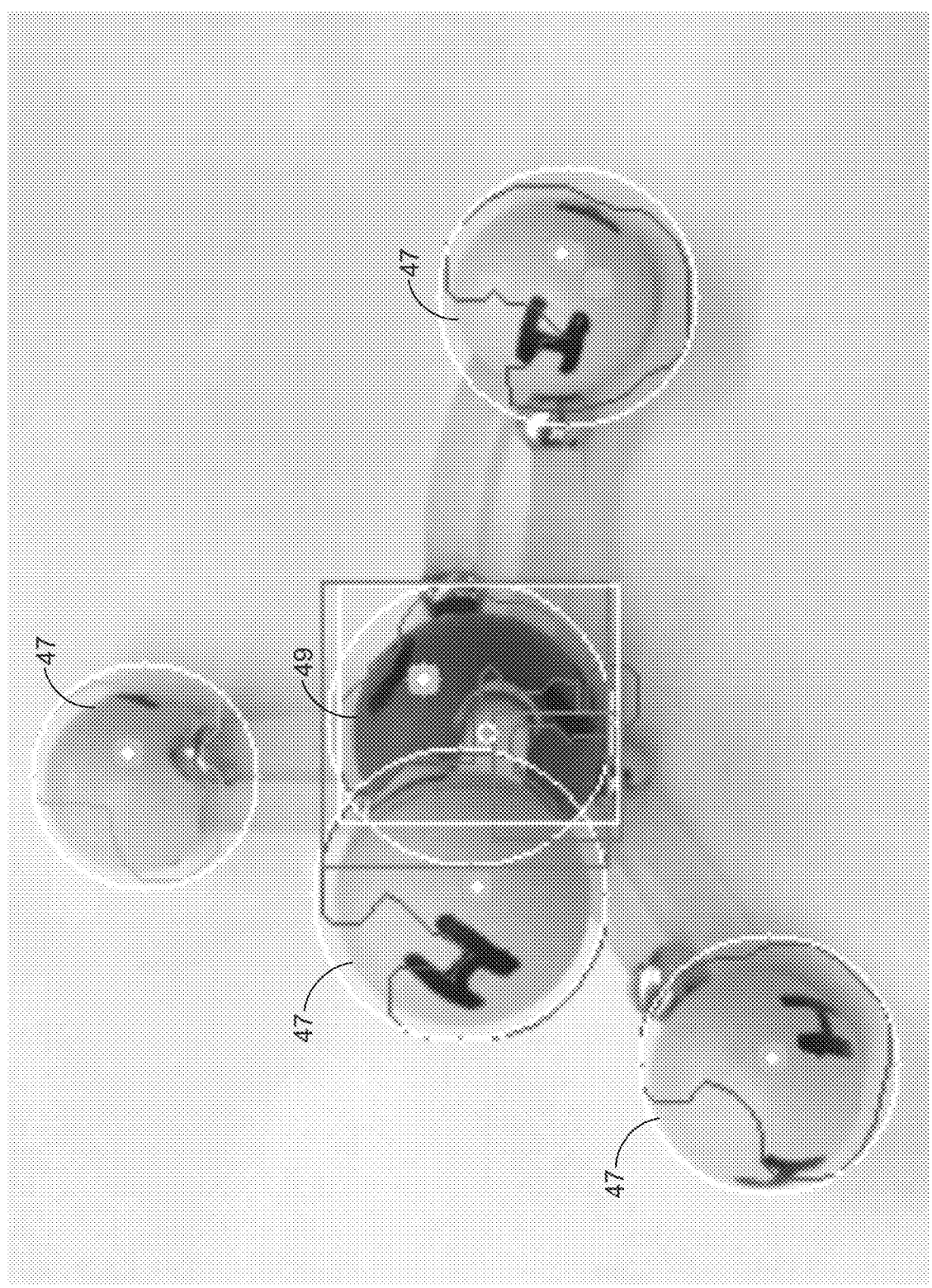

After the initial atom search is performed across the various color regions, one or more accuracy checks can be performed against the found atoms. An initial size test can be performed against the found atoms based on the estimated size found previously during processing of the algorithm 704. A circle-in-circle test can then be performed to remove atoms that are considered to be overlapping. In one example, red-pink circles can be given a special exception due to their unique relationship. Pink-red circles can be given a test to differentiate possible misidentifications and overlaps. The physical model may involve the assumption that pink circles should on average be smaller than red circles. This assumption allows larger pink circles or smaller red circles to be recategorized accordingly. FIG. 17 illustrates an example of how pink and red colored atoms 47, 49 can be differentiated based on their unique colors.

Figure 18:
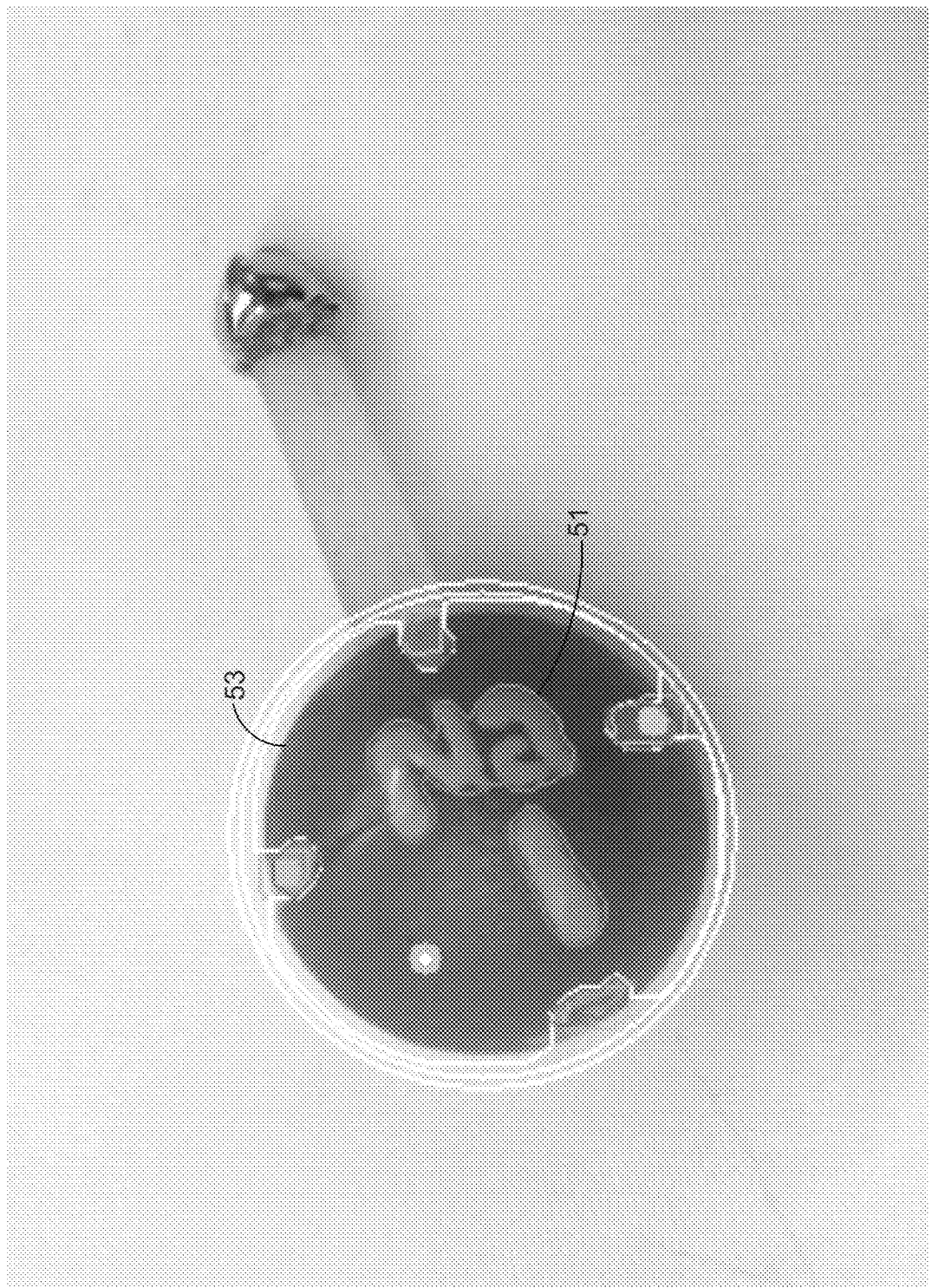

In this example, certain atoms such as those located in the third and fourth row of the period table of elements can be sought by looking for secondary colors found within the identified atom contour. As described above, each atom within a model may have its elemental indicia positioned on the nucleus structure. In many cases this text is colored black, but for the third and fourth row elements (e.g., sodium through chlorine) the text may be colored with a non-black color. This color may be chosen as a contrast or complement to the primary base color for the nucleus of the atom. If a predetermined percentage of this contrasting or complementary color is found during the analysis, then the atom can be recategorized at this point. FIG. 18 illustrates an example of indicia 51 for sodium colored differently (e.g., orange) in comparison to the nucleus 53 (e.g., blue). In certain embodiments, elements in the first and second rows of the periodic table may be likewise analyzed, including non-black colored text in association with a CPK coloring scheme, for example.

At action 818, the found set of atoms can be categorized and searched against a prefiltered database of atoms and molecules associated with the computer-implemented application of the modeling system.

From the foregoing, it can be seen that applying best-fit scenarios provides a greater level of accuracy for detecting atoms. Also, using multiple shape-detection algorithms that combine detected shapes in multiple ways can be effective for identifying the best atom fit. Ranged color-detection can be used to search for color ranges and to combine like colors into multiple fits. To address the problem that colors and shapes may blend together depending on both perspective and the camera angle used to take the initial picture, the algorithm 704 has the ability to determine whether a single, large area is a better fit when split into two (or more) separate shapes. In addition, the initial best-guess estimate can be employed at multiple points throughout the detection process, reducing the amount of error in the recognition.

It is desirable for the algorithm 704 to detect and identify molecules within a reasonable time frame and across a range of devices with differing computing power. To assist with processing time, threading can be employed with vision detection to speed up the process. At specific points in the processing of the algorithm 704, multiple tasks can be performed in parallel rather than waiting for a single task to finish (e.g., during the initial color sweeps of the image). Resizing of the image used for detection can also be implemented at specific points to promote greater speed without reducing accuracy.

Figure 19:
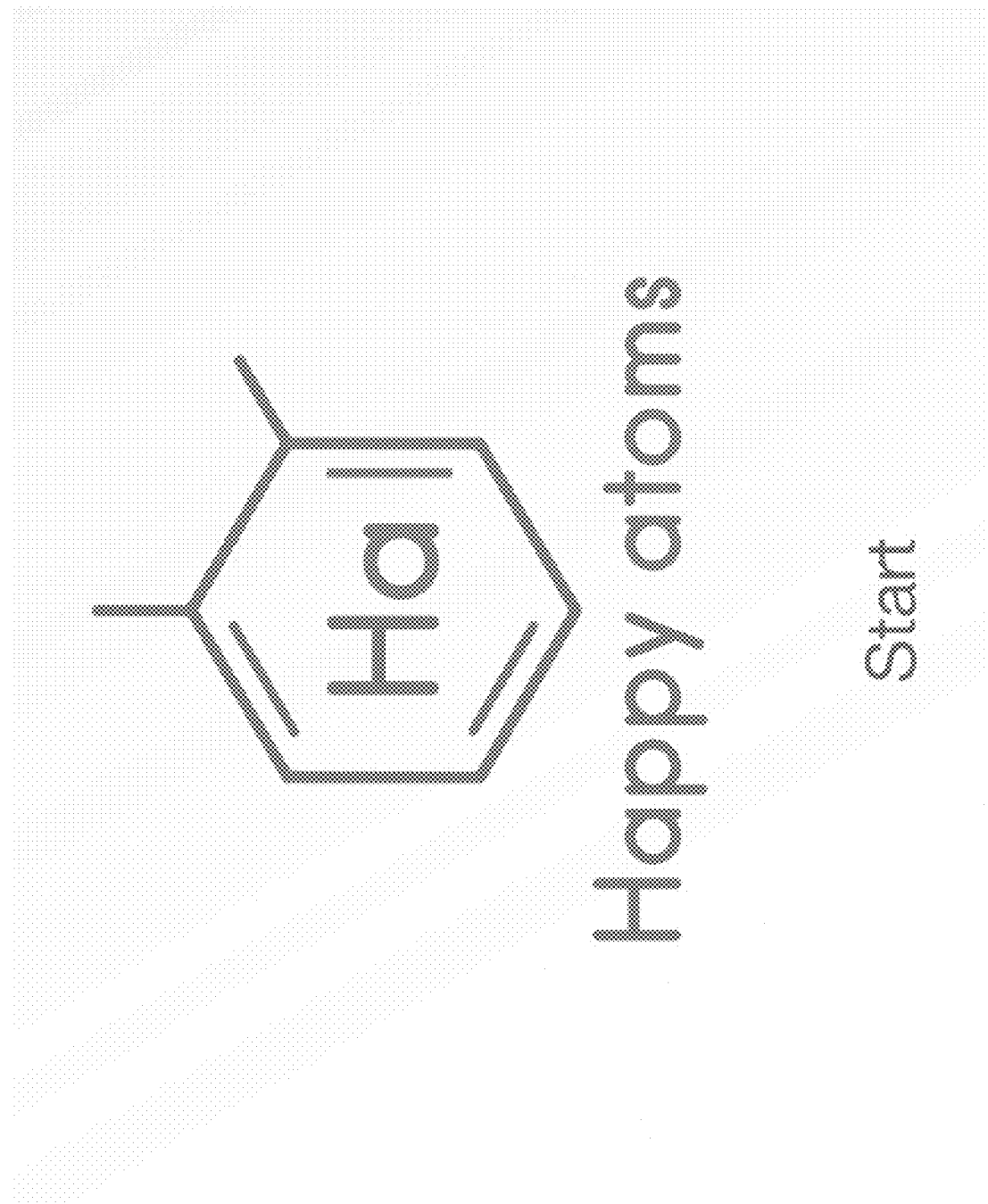
FIGS. 19 through 27 illustrate various aspects of an example of an application which can be programmed to execute a vision detection and analysis algorithm and provide information related to atoms and molecules.
Figure 20:
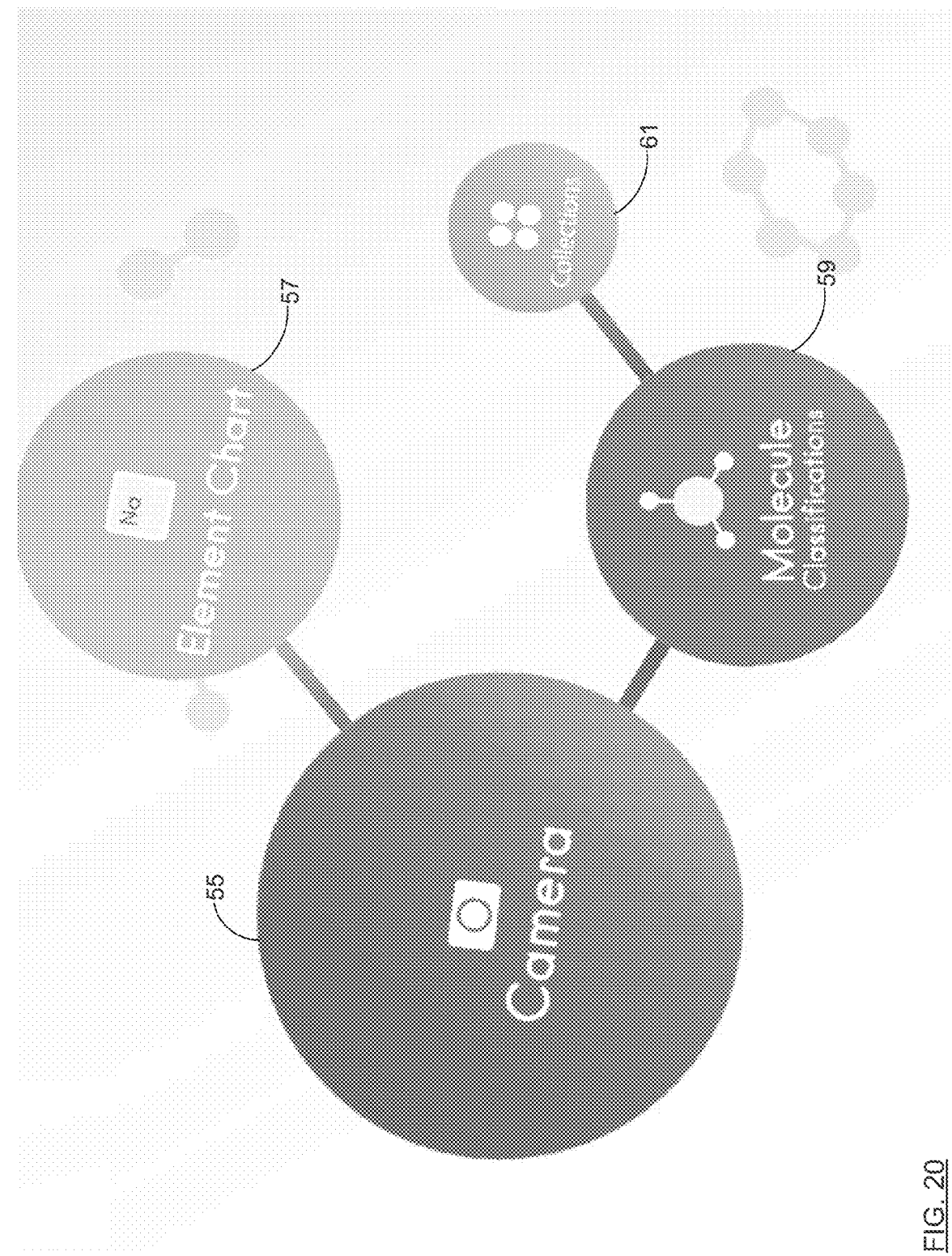
Figure 21:
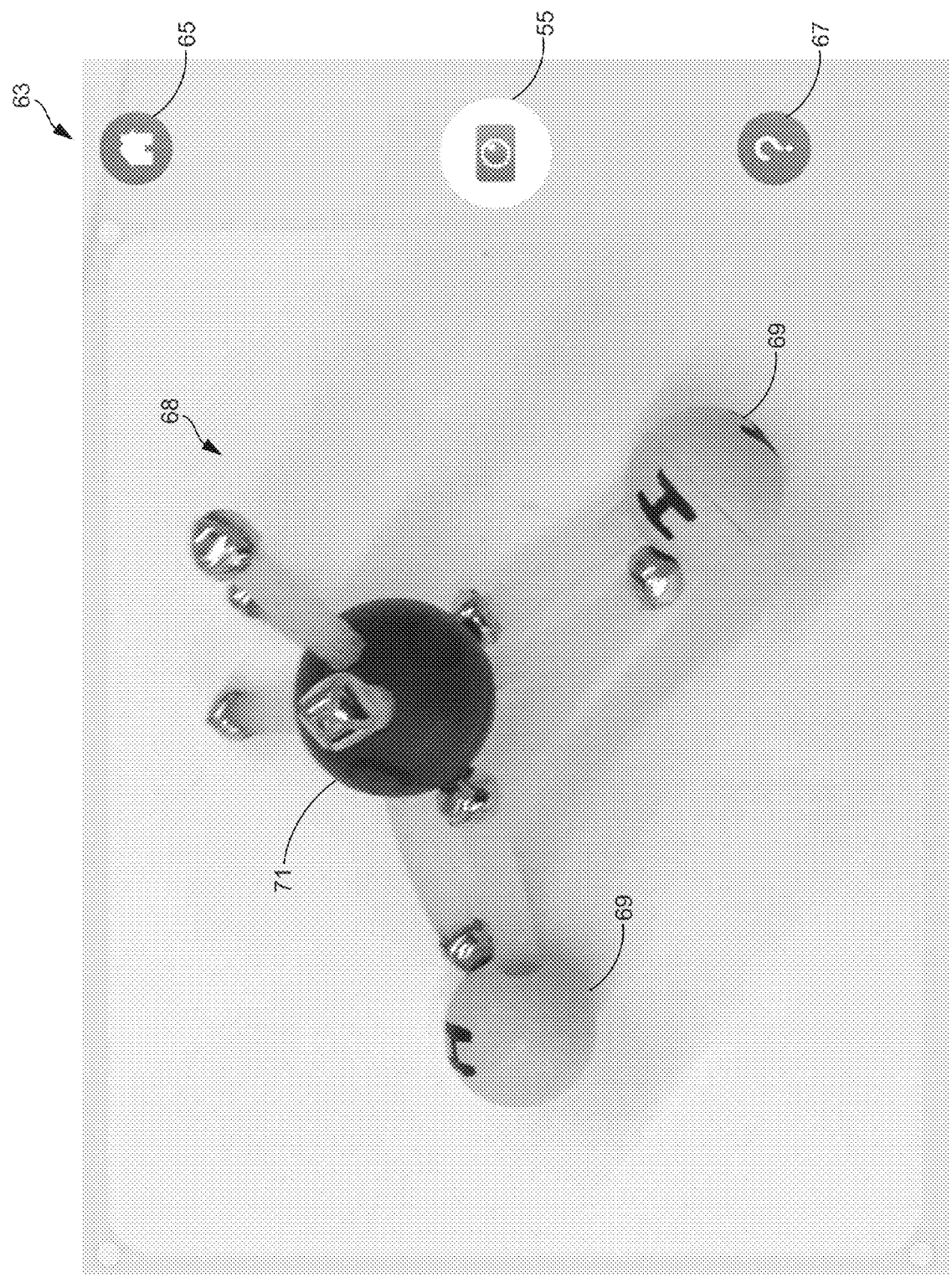

In one operational example of certain embodiments of the invention, FIG. 19 illustrates an example of an opening screen which can be presented to a user within the computer-implemented application of the modeling system. The user taps "Start" and is presented with the menu screen shown in FIG. 20, including the options of "Camera" button 55, "Element Chart" button 57, "Molecule Classification" button 59, and "Collections" button 61 among other functionality. When the user taps the "Camera" button 55, the camera capture screen 63 appears as shown in the example of FIG. 21. The user can take a photo of a molecular model 68 by tapping the camera button 55. Prior to taking the photo, a view of the molecular model 68 can be positioned within a frame or guide of the camera (e.g., inside the greyed-out border) to make sure the various atoms are visible to the camera. Additional functionality may include the option to return to the main menu by tapping the red home button 65 or obtain additional instructions by tapping the red question-mark button 67.

Figure 22:
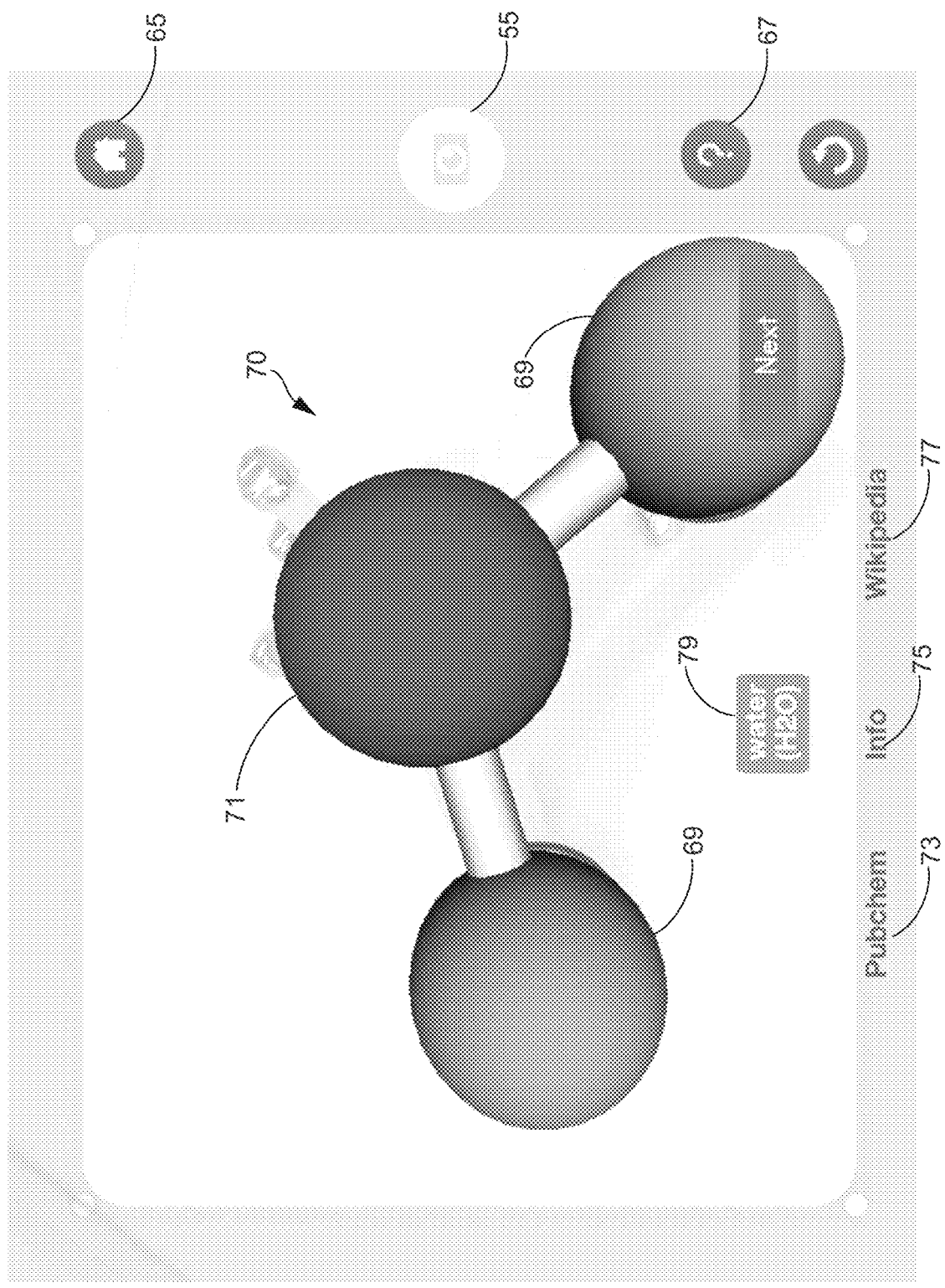
Figure 23:
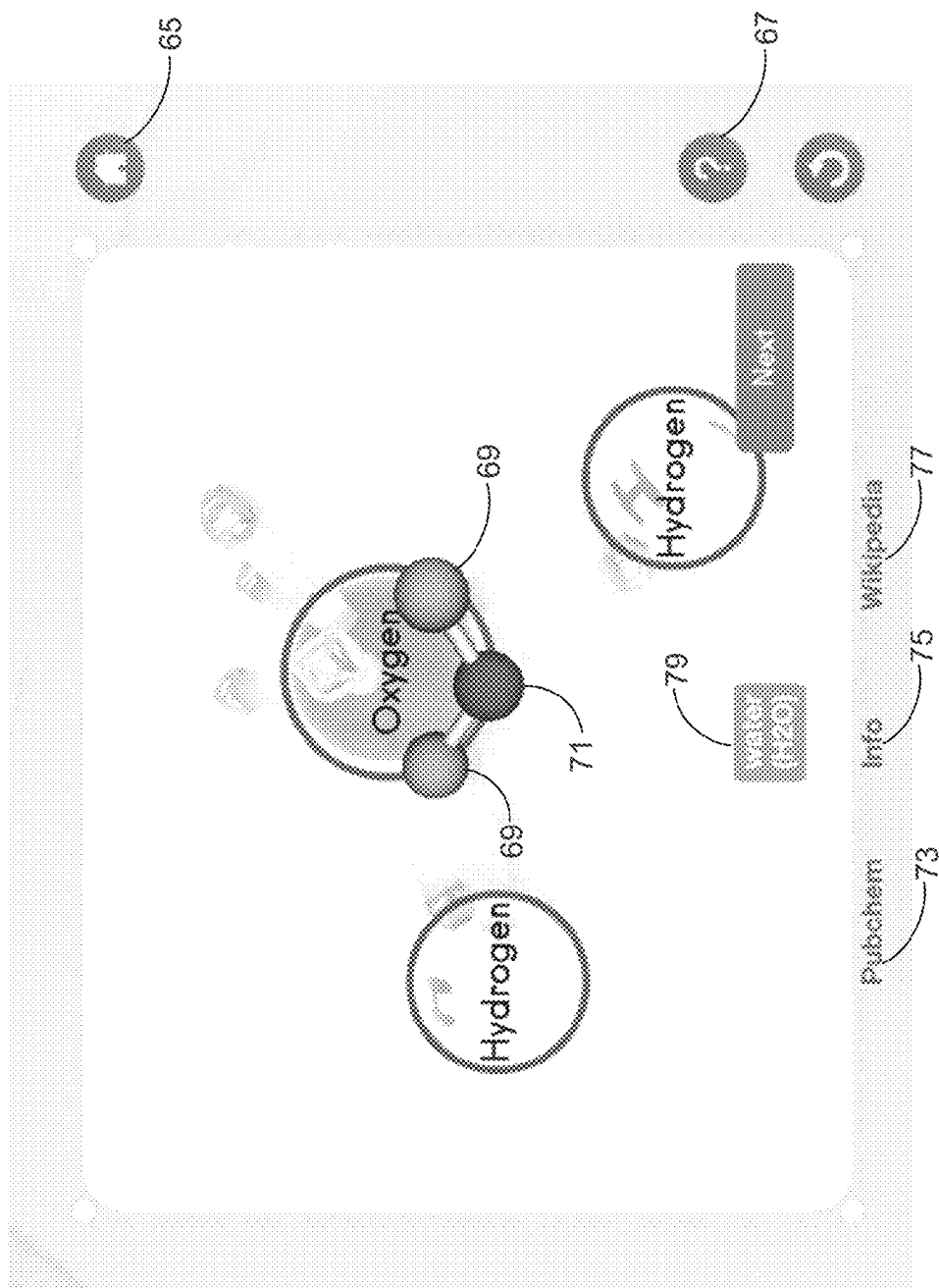

After the image of the molecular model 68 is captured, the application executes a vision detection and analysis algorithm to identify each atom (e.g., two hydrogens 69 and one oxygen 71) in the model 68. An example of this identification 79 is shown in FIGS. 22 and 23. It can be seen that the application can also provide a three-dimensional, rotating model 70 of the molecule represented by the model 70 along with its chemical formula and common name. The user may tap the "Pubchem", "Info", or "Wikipedia" links 73, 75, 77 at the bottom of the screen to obtain additional information about the molecule. Molecules identified by the user can be stored in a history collection which connects online to a chemistry content database that can be searched (e.g., "PubChem") or offline to a database of molecules stored by the application. The "Pubchem" and "Wikipedia" links 73, 77 may link directly through an Internet connection to their respective websites. The "Info" link 75 may connect to a database of selected molecules developed for use with the application. The purpose of this database is to promote access to additional information about selected common molecules, such as in the absence of an Internet connection required for "Pubchem" and "Wikipedia", for example.

Figure 24:
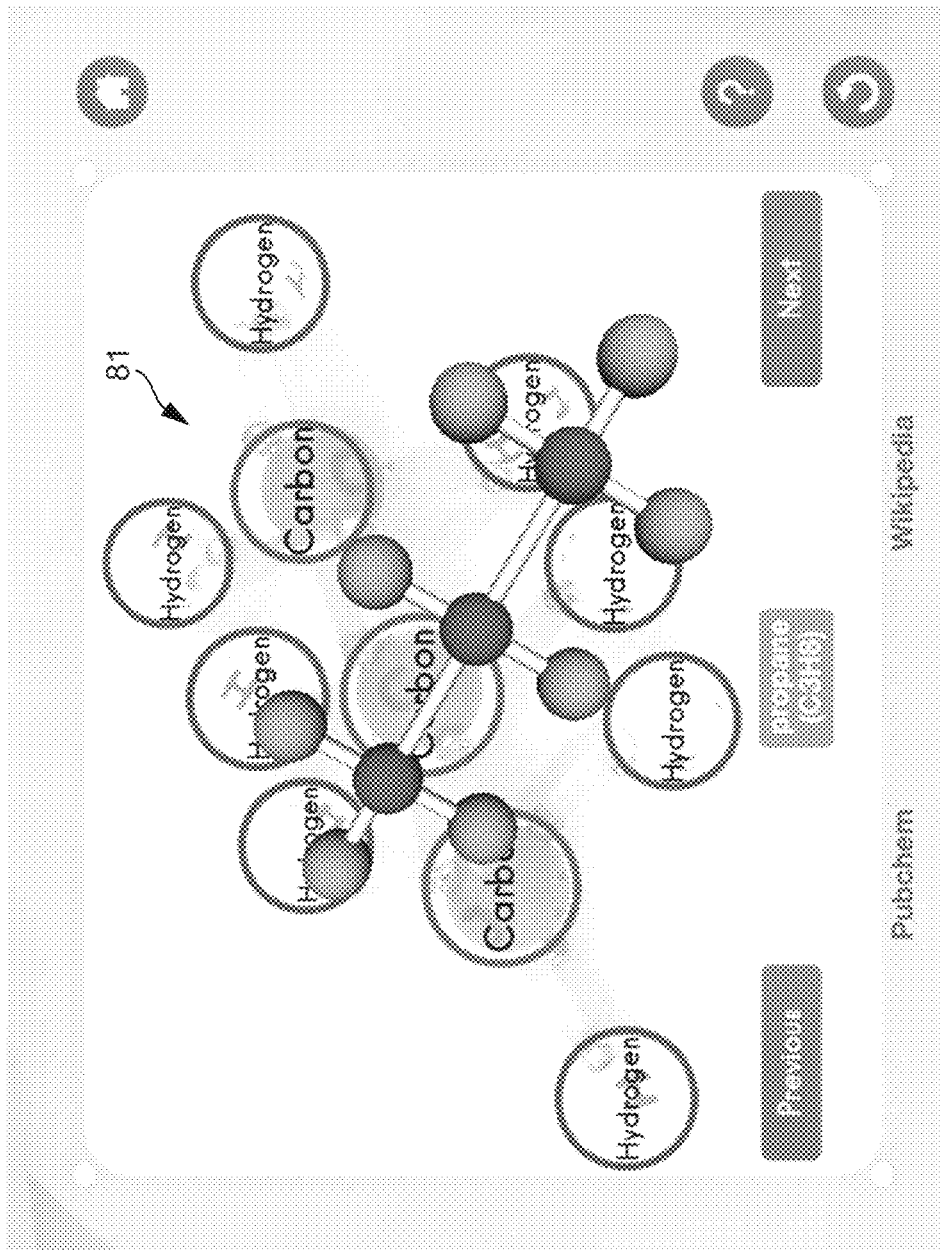
Figure 25:
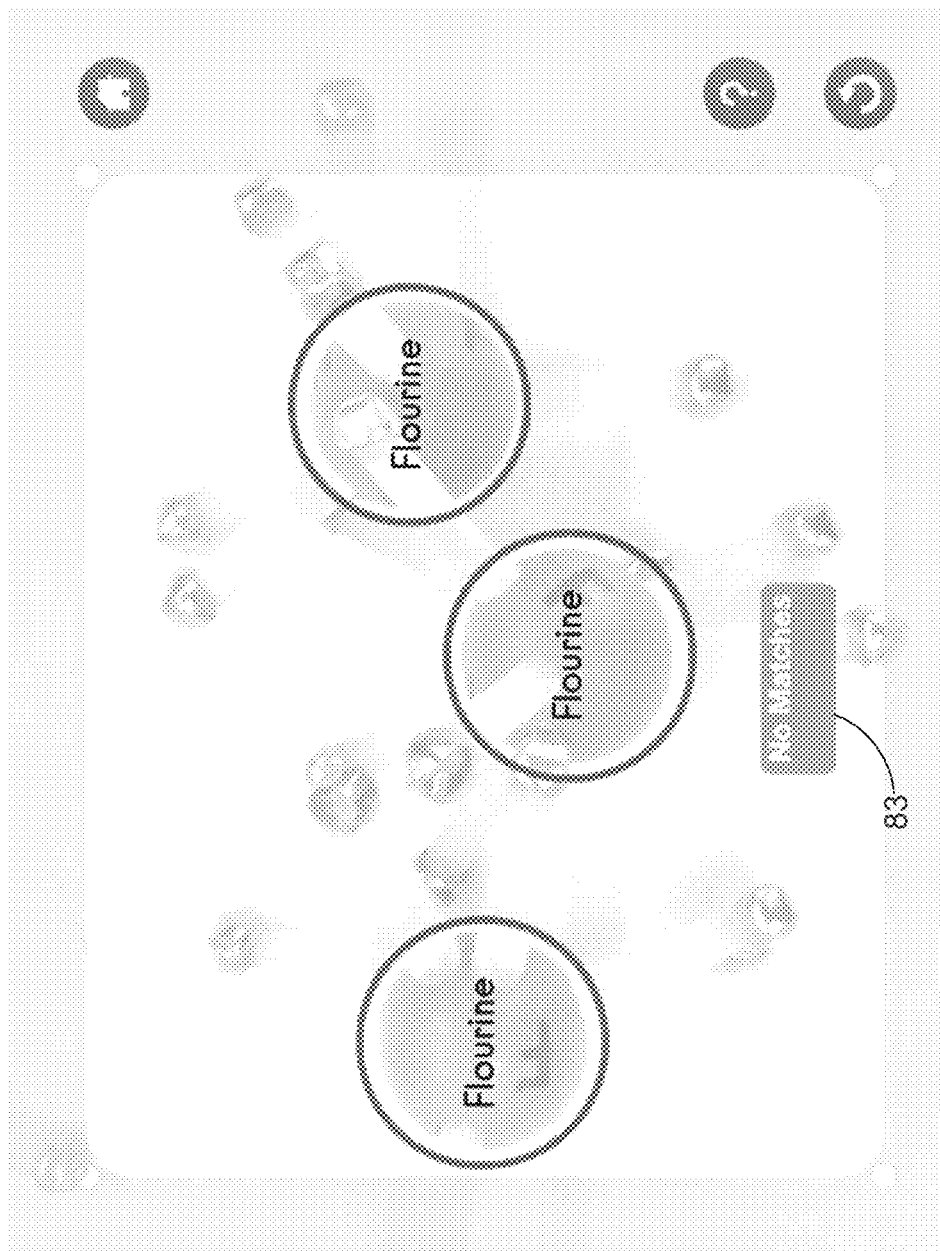

In the example shown in FIG. 24, it can be seen that the application can accommodate a wide range of molecule sizes. The propane molecule 81 shown in FIG. 24 can be easily identified despite its larger size compared to the water molecule. If a user fails to create a molecule (e.g., by creating a combination that does not exist or by incorrectly constructing the molecular model), the atoms may still be identified but the text "No Matches" 83 is displayed. An example of this identification is shown in FIG. 25.

Figure 26:
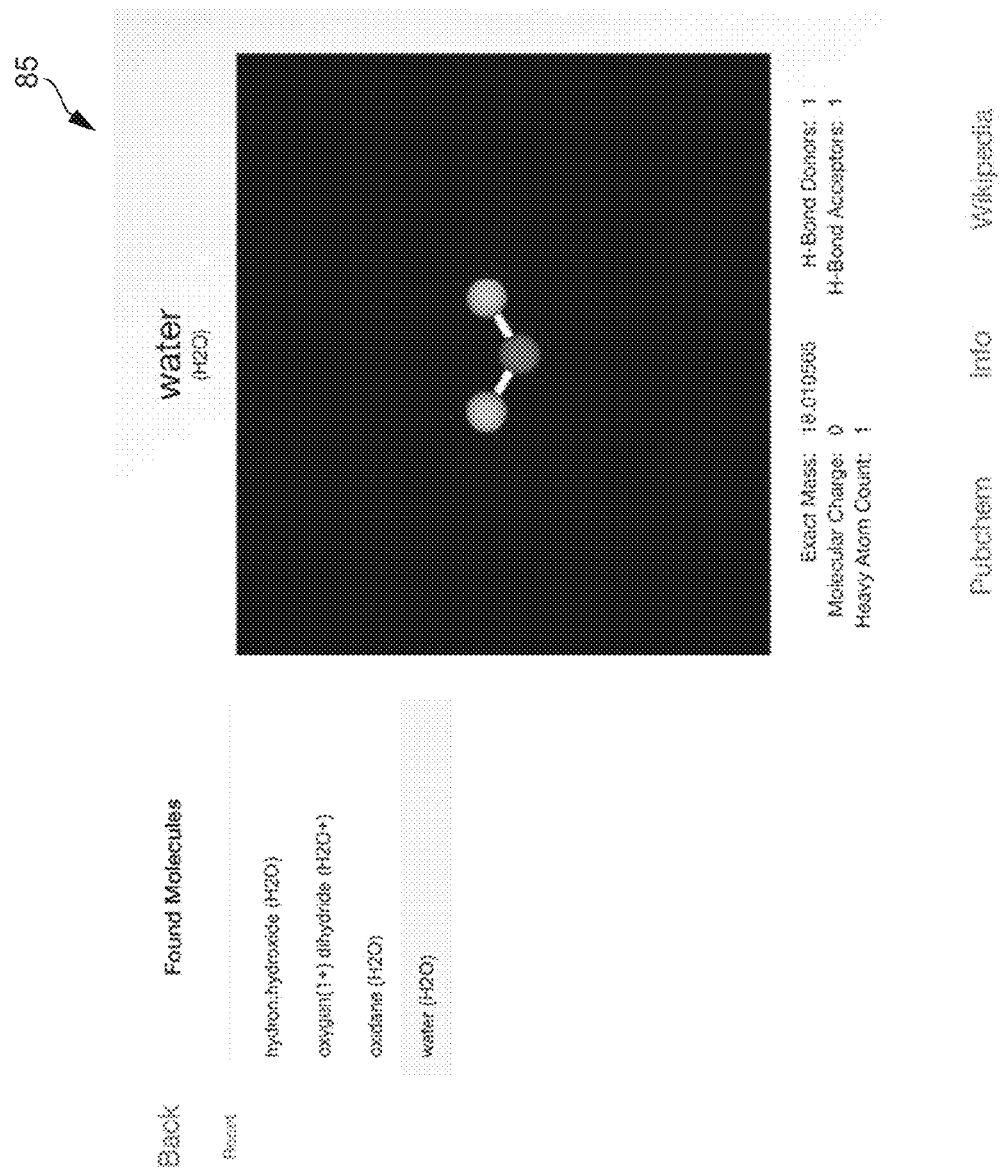

When the user returns to the main menu, the "Molecule Classification" section may be visited to see the molecules that have been found, along with their three-dimensional models and associated information screens. An example of the "Molecule Classification" section screen 85 is shown in FIG. 26.

Figure 27:
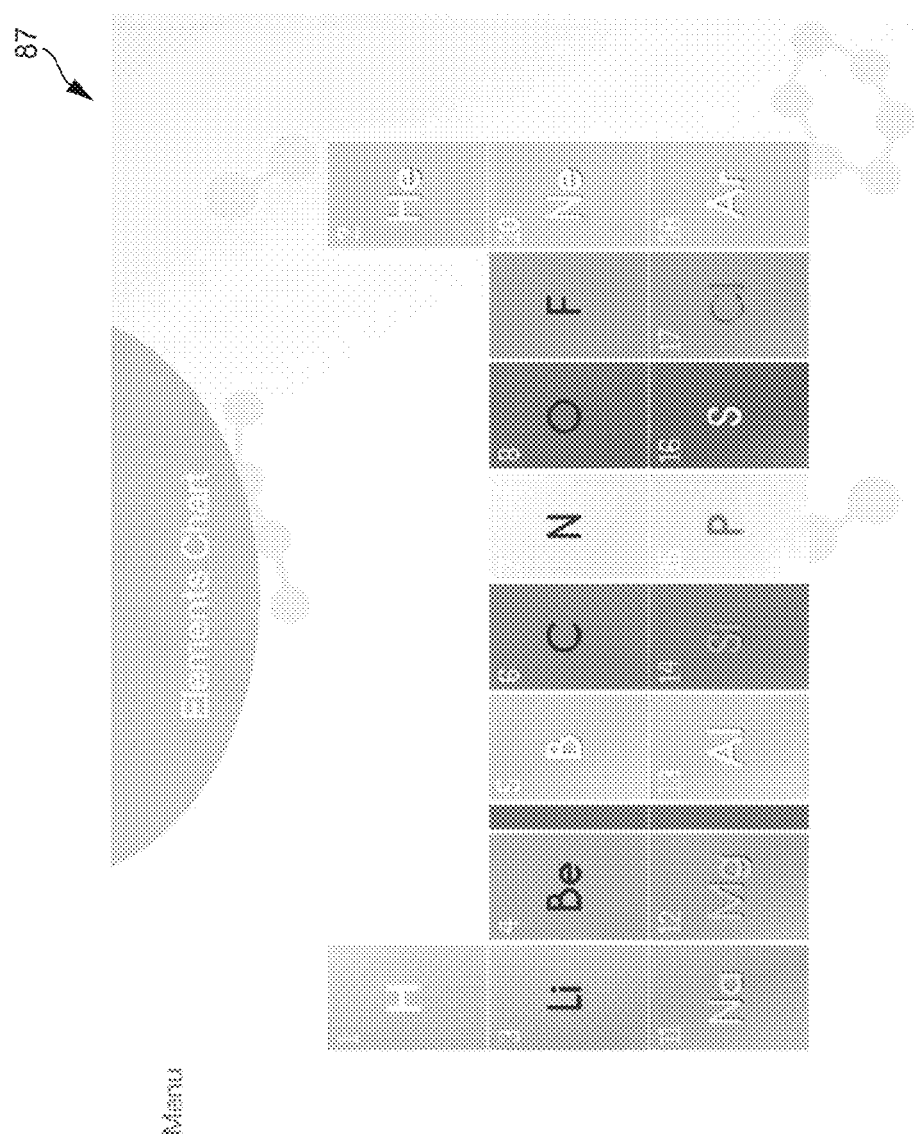

In this operational example, the user may also visit the "Periodic Chart" section to see a colorful rendering of the classic periodic table of elements. The colors on the chart may be configured to match the colors of the physical atomic models. An example of the "Periodic Chart" section screen display 87 is shown in FIG. 27.

In other aspects of the invention, an area may be included in the application dedicated to teacher resources, which might include suggestions on how to incorporate the modeling system into currently existing lesson plans, how to structure a class period while using the modeling system, suggested activities for specific concepts, and bonus activities for group work in the classroom. This can help teachers integrate the modeling system into their currently existing lesson plans. Games and activities can be provided to supplement the features of the application by taking a picture and discovering what molecule has been made, and then learning more about it via links and supplemental information pages.

Guided discovery activities may also be incorporated, which include but are not limited to molecule cards, interactive books, and chemistry stories.

Molecule cards can provide an activity containing boxes that can be unlocked by creating different molecules with the modeling set. Each box can be titled by a category or property, such as hydroxyls, acids, or flammable. When a user discovers something by building it with the modeling system, that discovery can be highlighted in the corresponding box. Some molecules may reside in more than one box. By activating a box, the user can start to discover other molecules that exist within the same category. The activity may give hints about how to create the other molecules in that box, or may give more information about the particular properties of the box. Boxes can also contain different activities, including videos of particular molecules or elements, as well as reaction boxes, which provide the basics of balancing equations by showing the reactants or products of a reaction and asking the user to find the missing molecules. Molecules can be categorized according to familiarity (e.g., "Not Discovered," "Seen it," and "Made it") to cover all isomers or other versions of a molecule which creates a collection utility to encourage more building.

Interactive books may include a set of activities that use a subset of elements from the modeling system to guide the user through exercises to gain familiarity with the modeling system. An example of this activity is introducing the user to the carbon, hydrogen, and oxygen atoms, and then asking the user to connect them together to form simple molecules, such as methane and oxygen gas. The user can then progress to a guided experiment with a simple combustion reaction, asking the user to break apart their molecules to form water and find what other products are created. These interactive books could cover a wide range of topics, including combustion, acid and base reactions, and many others. These could also be condensed into the interactive cards in the molecule cards activity described above.

Chemistry stories involve answering real-life questions by explaining them with chemistry. Examples of stories could explain why rock salt helps melt ice, why something is flammable, and why dyes affect some materials but not others. These questions may utilize text, diagrams, videos, and the modeling system to explain these real-life problems in an interactive and engaging manner.

Figure 28:
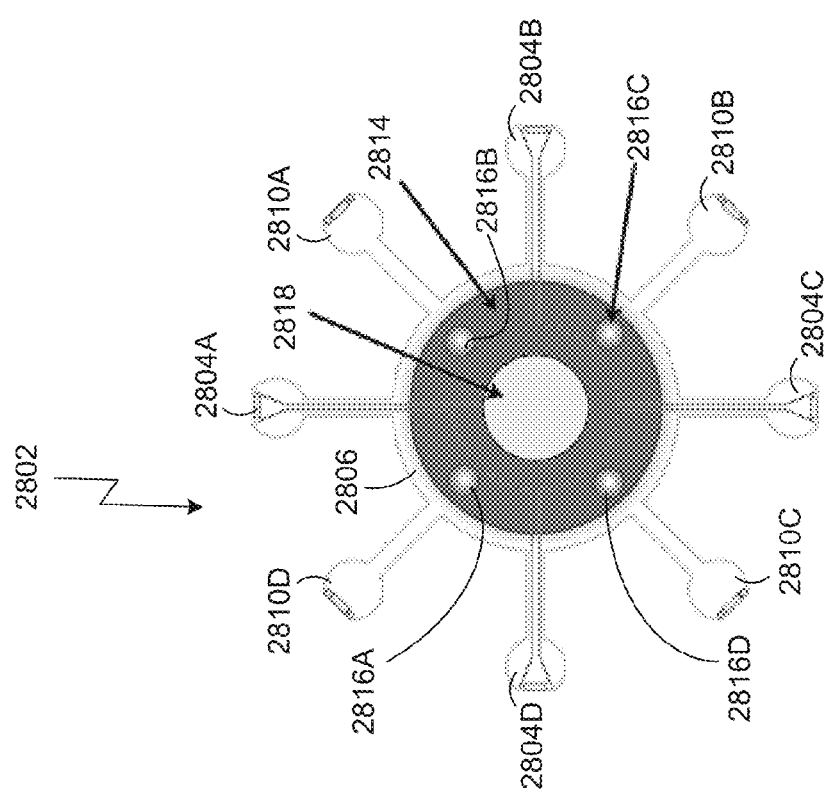
FIG. 28 shows an example of an atomic model configured to present visual cues to a user.

With reference to FIG. 28, another example of an atomic model 2802 is provided which has been configured to present visual cues to a user regarding the construction of the model 2802 and its interaction with one or more other atomic models. In this example, multiple bonding arms 2804A-2804D extend from a nucleus structure 2806 of the model, and these bonding arms 2804A-2804D represent various valence electrons associated with an atom represented by the model 2802. Also, multiple bonding arms 2810A-2810D extend from the nucleus structure 2806, and these bonding arms 2810A-2810D represent various electron holes associated with the atom represented by the model 2802. During use of the model 2802 with one or more other atomic models, such as to construct various molecular models, it can be seen that one or more of the valence electron bonding arms 2804A-2804D of the model 2802 can be configured for attachment (e.g., by magnetic means) to the electron hole bonding arms of one or more other atomic models. Likewise, one or more of the electron hole bonding arms 2810A-2810D of the model 2802 can be configured for attachment (e.g., by magnetic means) to the valence electron bonding arms of one or more other atomic models.

In various embodiments, and with additional reference to FIGS. 29A-30B, each of the bonding arms 2804A-2804D, 2810A-2810D can be provided with a magnet 2812 to serve as a connection point between the bonding arms of different atomic models. The electron valence bonding arms 2804A-2804D of the atomic model 2802 may be provided with electrical contact points 2902, 2904 wired to a printed circuit board 2814 located within the nucleus structure 2806. As shown in FIGS. 30A and 30B, the electron hole bonding arms 2810A-2810D may be provided with a metallic washer 2906 such as an aluminum washer, for example, which can establish contact with the electrical contact points 2902, 2904, such as when magnets 2812 are attracted and connected to each other during assembly of a molecular model, for example. The printed circuit board 2814 may include one or more lighting means 2816A-2816D (e.g., light-emitting diodes) which can be activated when one or more electrical circuits are completed in association with the interaction of the magnets 2812 at one or more of the bonding locations between valence electron bonding arms and electron hole bonding arms of different atomic models.

Figure 31:
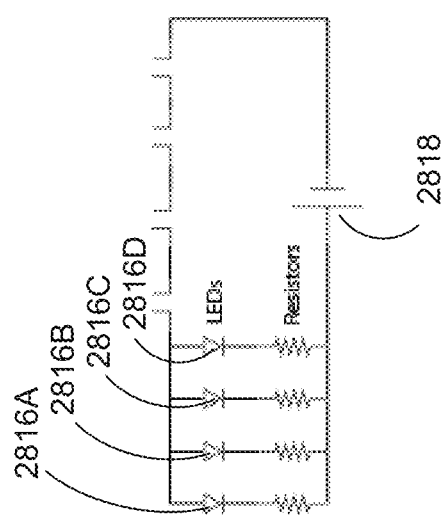
FIG. 31 shows an example of an electrical circuit schematic configured for use in association with presenting visual cues to a user.

The circuit schematic of FIG. 31 provides an example of requiring multiple such circuits to be completed to activate all of the lighting means 2816A-2816D on the printed circuit board 2814 within the nucleus structure 2806. It can be seen that this can provide a visual cue to a user that all of the valence electron bonding arms 2804A-2804D, for example, have been successfully connected to the electron hole bonding arms of one or more other models. In certain embodiments, the circuit may be configured to activate one or less than all of the lighting means 2816A-2816D, such as to communicate to a user that successful connection has been achieved for individual valence electron bonding arms 2804A-2804D. In various embodiments, the printed circuit board 2814 may be powered by a watch battery 2818, for example, or another suitable power source. In other embodiments, the lighting means 2816A-2816D could be replaced or supplemented with another connection communication means, such as components which create an audible indication or noise, or components which cause the nucleus structure 2806 to vibrate upon completion of one or more electrical connections. For example, one or more haptic motors may be employed in place of, or in combination with, one or more of the lighting means 2816A-2816D to create a vibration effect for a user during model assembly.

Figure 32:
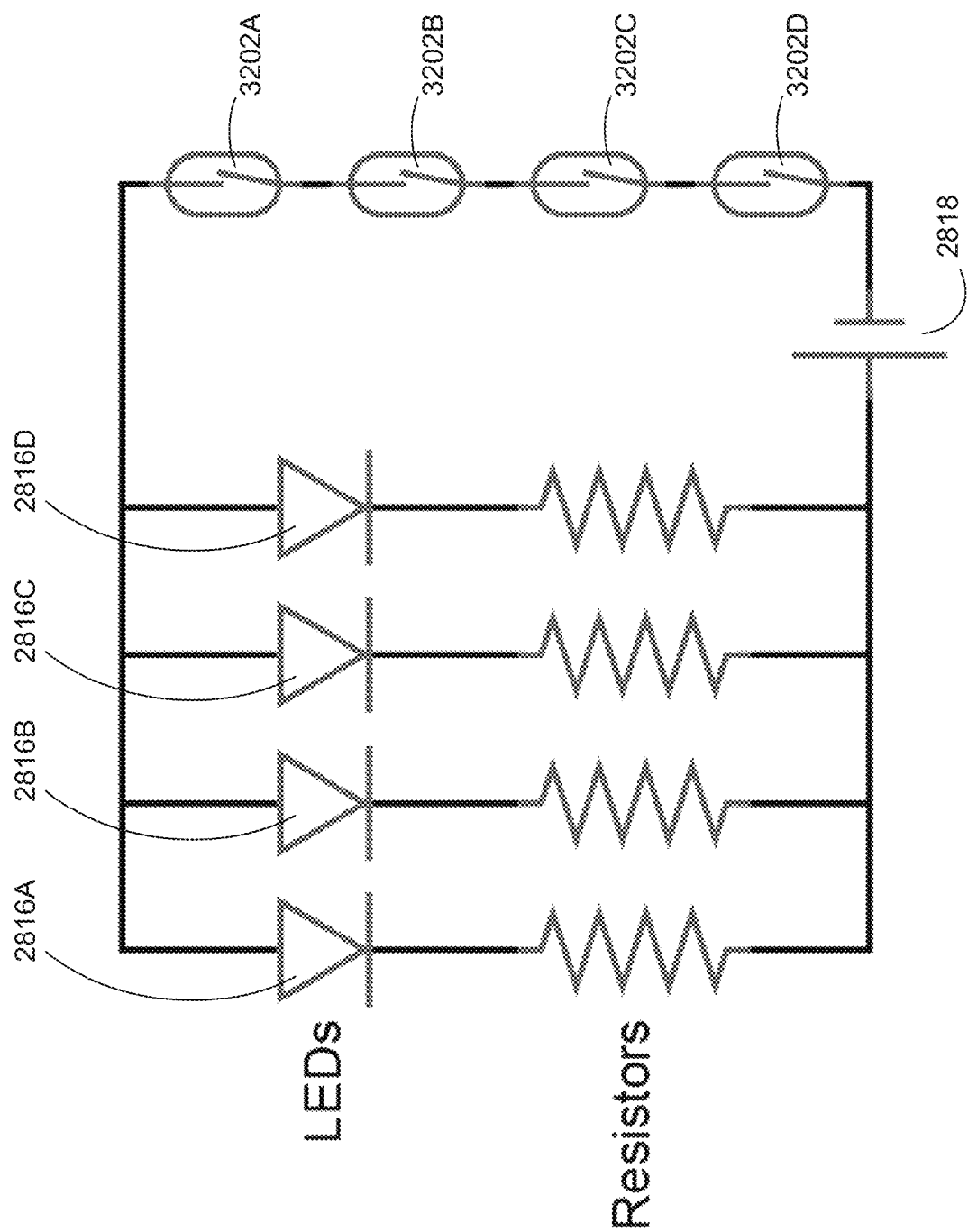
FIG. 32 shows an example of an electrical circuit schematic configured for use in association with presenting visual cues to a user; and, FIG. 33 illustrates various examples of atomic models which can be structured to operate in connection with certain embodiments of the invention.

With reference to FIG. 32, the electrical circuitry associated with the printed circuit board 2814 may include one or more switches 3202A-3202D activated by a magnetic field (e.g., a Reed switch or like switch). The switches 3202A-3202D may activate in response to a magnetic field generated when a connection is established between different magnets 2812, such as when a valence electron bonding arm and an electron hole bonding arm are connected, for example. As discussed above, the printed circuit board 2814 may include one or more lighting means 2816A-2816D (e.g., light-emitting diodes) which can be activated when one or more electrical circuits are completed by the interaction of the magnets 2812 at one or more of the bonding locations between valence electron bonding arms and electron hole bonding arms of different atomic models.

Figure 33:
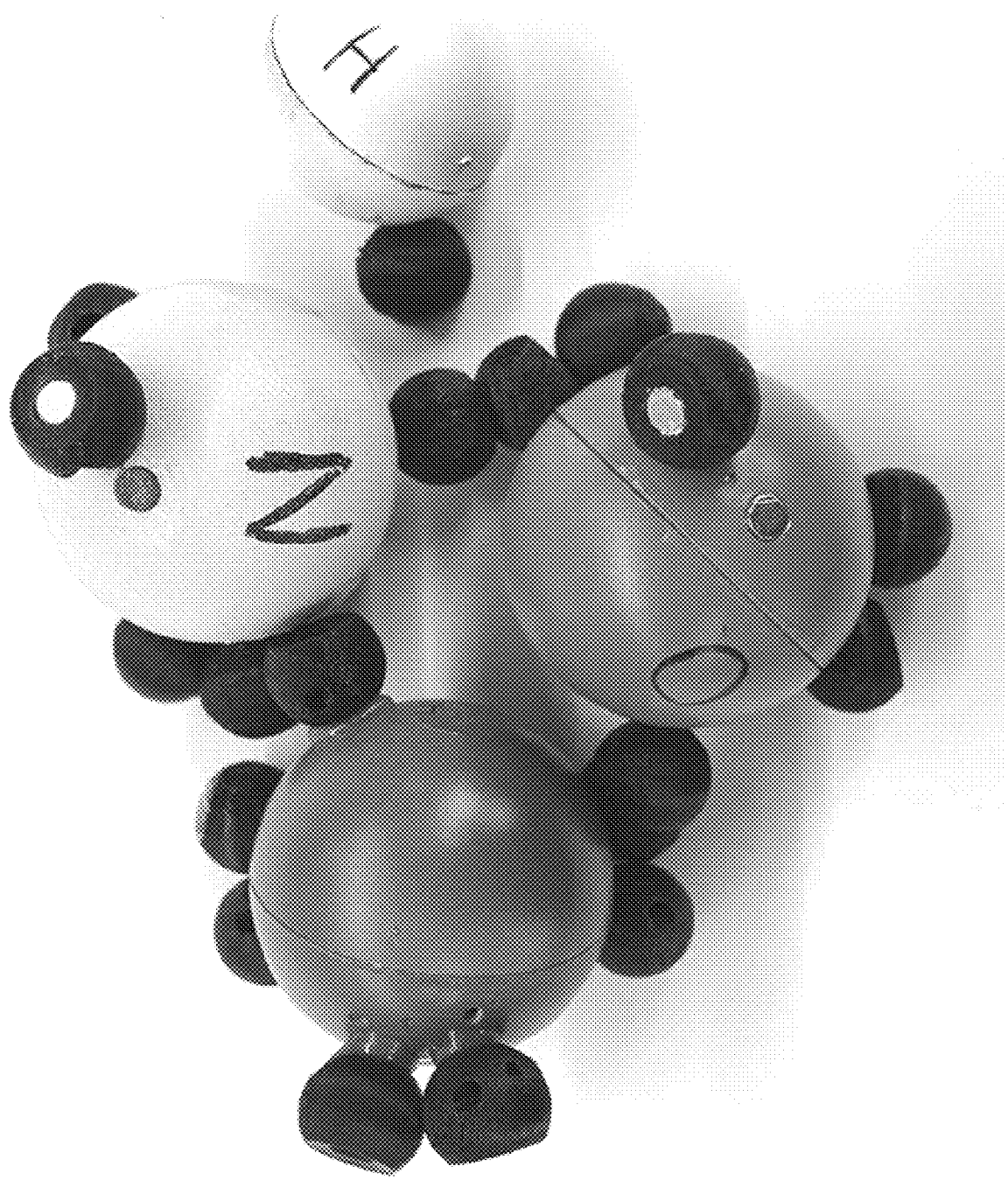

FIG. 33 illustrates various examples of models 89 which can be structured to operate in connection with the embodiments described above with regard to FIGS. 28 through 32.

The examples presented herein are intended to illustrate potential and specific implementations of the present invention. It can be appreciated that the examples are intended primarily for purposes of illustration of the invention for those skilled in the art. No particular aspect or aspects of the examples are necessarily intended to limit the scope of the present invention. For example, no particular aspect or aspects of the examples of system architectures, user interface layouts, or screen displays described herein are necessarily intended to limit the scope of the invention.

It is to be understood that the figures and descriptions of the present invention have been simplified to illustrate elements that are relevant for a clear understanding of the present invention, while eliminating, for purposes of clarity, other elements. Those of ordinary skill in the art will recognize, however, that a sufficient understanding of the present invention can be gained by the present disclosure, and therefore, a more detailed description of such elements is not provided herein.

Any element expressed herein as a means for performing a specified function is intended to encompass any way of performing that function including, for example, a combination of elements that performs that function. Furthermore the invention, as may be defined by such means-plus-function claims, resides in the fact that the functionalities provided by the various recited means are combined and brought together in a manner as defined by the appended claims. Therefore, any means that can provide such functionalities may be considered equivalents to the means shown herein.

In various embodiments, modules or software can be used to practice certain aspects of the invention. For example, software-as-a-service (SaaS) models or application service provider (ASP) models may be employed as software application delivery models to communicate software applications to clients or other users. Such software applications can be downloaded through an Internet connection, for example, and operated either independently (e.g., downloaded to a laptop or desktop computer system) or through a third-party service provider (e.g., accessed through a third-party web site). In addition, cloud computing techniques may be employed in connection with various embodiments of the invention. In certain embodiments, a "module" may include software, firmware, hardware, or any reasonable combination thereof.

Moreover, the processes associated with the present embodiments may be executed by programmable equipment, such as computers. Software or other sets of instructions that may be employed to cause programmable equipment to execute the processes may be stored in any storage device, such as a computer system (non-volatile) memory. Furthermore, some of the processes may be programmed when the computer system is manufactured or via a computer-readable memory storage medium.

It can also be appreciated that certain process aspects described herein may be performed using instructions stored on a computer-readable memory medium or media that direct a computer or computer system to perform process steps. A computer-readable medium may include, for example, memory devices such as diskettes, compact discs of both read-only and read/write varieties, optical disk drives, and hard disk drives. A computer-readable medium may also include memory storage that may be physical, virtual, permanent, temporary, semi-permanent and/or semi-temporary. Memory and/or storage components may be implemented using any computer-readable media capable of storing data such as volatile or non-volatile memory, removable or non-removable memory, erasable or non-erasable memory, writeable or re-writeable memory, and so forth. Examples of computer-readable storage media may include, without limitation, RAM, dynamic RAM (DRAM), Double-Data-Rate DRAM (DDRAM), synchronous DRAM (SDRAM), static RAM (SRAM), read-only memory (ROM), programmable ROM (PROM), erasable programmable ROM (EPROM), electrically erasable programmable ROM (EEPROM), flash memory (e.g., NOR or NAND flash memory), content addressable memory (CAM), polymer memory (e.g., ferroelectric polymer memory), phase-change memory, ovonic memory, ferroelectric memory, silicon-oxide-nitride-oxide-silicon (SONOS) memory, magnetic or optical cards, or any other type of media suitable for storing information.

A "computer," "computer system," "computing apparatus," "component," or "computer processor" may be, for example and without limitation, a processor, microcomputer, minicomputer, server, mainframe, laptop, personal data assistant (PDA), wireless e-mail device, smart phone, mobile phone, electronic tablet, cellular phone, pager, processor, fax machine, scanner, or any other programmable device or computer apparatus configured to transmit, process, and/or receive data. Computer systems and computer-based devices disclosed herein may include memory and/or storage components for storing certain software applications used in obtaining, processing, and communicating information. It can be appreciated that such memory may be internal or external with respect to operation of the disclosed embodiments. In various embodiments, a "host," "engine," "loader," "filter," "platform," or "component" may include various computers or computer systems, or may include a reasonable combination of software, firmware, and/or hardware.

In general, it will be apparent to one of ordinary skill in the art that various embodiments described herein, or components or parts thereof, may be implemented in many different embodiments of software, firmware, and/or hardware, or modules thereof. The software code or specialized control hardware used to implement some of the present embodiments is not limiting of the present invention. For example, the embodiments described hereinabove may be implemented in computer software using any suitable computer programming language such as .NET, SQL, MySQL, or HTML using, for example, conventional or object-oriented techniques. Programming languages for computer software and other computer-implemented instructions may be translated into machine language by a compiler or an assembler before execution and/or may be translated directly at run time by an interpreter. Examples of assembly languages include ARM, MIPS, and x86; examples of high level languages include Ada, BASIC, C, C++, C#, COBOL, Fortran, Java, Lisp, Pascal, Object Pascal; and examples of scripting languages include Bourne script, JavaScript, Python, Ruby, PHP, and Perl. Various embodiments may be employed in a Lotus Notes environment, for example. Such software may be stored on any type of suitable computer-readable medium or media such as, for example, a magnetic or optical storage medium. Thus, the operation and behavior of the embodiments are described without specific reference to the actual software code or specialized hardware components. The absence of such specific references is feasible because it is clearly understood that artisans of ordinary skill would be able to design software and control hardware to implement the embodiments of the present invention based on the description herein with only a reasonable effort and without undue experimentation.

Various embodiments of the systems and methods described herein may employ one or more electronic computer networks to promote communication among different components, transfer data, or to share resources and information. Such computer networks can be classified according to the hardware and software technology that is used to interconnect the devices in the network, such as optical fiber, Ethernet, wireless LAN, HomePNA, power line communication or G.hn. The computer networks may also be embodied as one or more of the following types of networks: local area network (LAN); metropolitan area network (MAN); wide area network (WAN); virtual private network (VPN); storage area network (SAN); or global area network (GAN), among other network varieties.

For example, a WAN computer network may cover a broad area by linking communications across metropolitan, regional, or national boundaries. The network may use routers and/or public communication links. One type of data communication network may cover a relatively broad geographic area (e.g., city-to-city or country-to-country) which uses transmission facilities provided by common carriers, such as telephone service providers. In another example, a GAN computer network may support mobile communications across multiple wireless LANs or satellite networks. In another example, a VPN computer network may include links between nodes carried by open connections or virtual circuits in another network (e.g., the Internet) instead of by physical wires. The link-layer protocols of the VPN can be tunneled through the other network. One VPN application can promote secure communications through the Internet. The VPN can also be used to separately and securely conduct the traffic of different user communities over an underlying network. The VPN may provide users with the virtual experience of accessing the network through an IP address location other than the actual IP address which connects the access device to the network.

The computer network may be characterized based on functional relationships among the elements or components of the network, such as active networking, client-server, or peer-to-peer functional architecture. The computer network may be classified according to network topology, such as bus network, star network, ring network, mesh network, star-bus network, or hierarchical topology network, for example. The computer network may also be classified based on the method employed for data communication, such as digital and analog networks.

Embodiments of the methods and systems described herein may employ internetworking for connecting two or more distinct electronic computer networks or network segments through a common routing technology. The type of internetwork employed may depend on administration and/or participation in the internetwork. Non-limiting examples of internetworks include intranet, extranet, and Internet. Intranets and extranets may or may not have connections to the Internet. If connected to the Internet, the intranet or extranet may be protected with appropriate authentication technology or other security measures. As applied herein, an intranet can be a group of networks which employ Internet Protocol, web browsers and/or file transfer applications, under common control by an administrative entity. Such an administrative entity could restrict access to the intranet to only authorized users, for example, or another internal network of an organization or commercial entity. As applied herein, an extranet may include a network or internetwork generally limited to a primary organization or entity, but which also has limited connections to the networks of one or more other trusted organizations or entities (e.g., customers of an entity may be given access to an intranet of the entity thereby creating an extranet).

Computer networks may include hardware elements to interconnect network nodes, such as network interface cards (NICs) or Ethernet cards, repeaters, bridges, hubs, switches, routers, and other like components. Such elements may be physically wired for communication and/or data connections may be provided with microwave links (e.g., IEEE 802.12) or fiber optics, for example. A network card, network adapter or NIC can be designed to allow computers to communicate over the computer network by providing physical access to a network and an addressing system through the use of MAC addresses, for example. A repeater can be embodied as an electronic device that receives and retransmits a communicated signal at a boosted power level to allow the signal to cover a telecommunication distance with reduced degradation. A network bridge can be configured to connect multiple network segments at the data link layer of a computer network while learning which addresses can be reached through which specific ports of the network. In the network, the bridge may associate a port with an address and then send traffic for that address only to that port. In various embodiments, local bridges may be employed to directly connect local area networks (LANs); remote bridges can be used to create a wide area network (WAN) link between LANs; and/or, wireless bridges can be used to connect LANs and/or to connect remote stations to LANs.

In various embodiments, a hub may be employed which contains multiple ports. For example, when a data packet arrives at one port of a hub, the packet can be copied unmodified to all ports of the hub for transmission. A network switch or other devices that forward and filter OSI layer 2 datagrams between ports based on MAC addresses in data packets can also be used. A switch can possess multiple ports, such that most of the network is connected directly to the switch, or another switch that is in turn connected to a switch. The term "switch" can also include routers and bridges, as well as other devices that distribute data traffic by application content (e.g., a Web URL identifier). Switches may operate at one or more OSI model layers, including physical, data link, network, or transport (i.e., end-to-end). A device that operates simultaneously at more than one of these layers can be considered a multilayer switch. In certain embodiments, routers or other like networking devices may be used to forward data packets between networks using headers and forwarding tables to determine an optimum path through which to transmit the packets.

Embodiments of the methods and systems described herein may divide functions between separate CPUs, creating a multiprocessing configuration. For example, multiprocessor and multi-core (multiple CPUs on a single integrated circuit) computer systems with co-processing capabilities may be employed. Also, multitasking may be employed as a computer processing technique to handle simultaneous execution of multiple computer programs.

In various embodiments, the computer systems, data storage media, or modules described herein may be configured and/or programmed to include one or more of the above-described electronic, computer-based elements and components, or computer architecture. In addition, these elements and components may be particularly configured to execute the various rules, algorithms, programs, processes, and method steps described herein.

Various embodiments may be described herein in the general context of computer executable instructions, such as software, program modules, and/or engines being executed by a computer. Generally, software, program modules, and/or engines include any software element arranged to perform particular operations or implement particular abstract data types. Software, program modules, and/or engines can include routines, programs, objects, components, data structures and the like that perform particular tasks or implement particular abstract data types. An implementation of the software, program modules, and/or engines components and techniques may be stored on and/or transmitted across some form of computer-readable media. In this regard, computer-readable media can be any available medium or media usable to store information and accessible by a computing device. Some embodiments also may be practiced in distributed computing environments where operations are performed by one or more remote processing devices that are linked through a communications network. In a distributed computing environment, software, program modules, and/or engines may be located in both local and remote computer storage media including memory storage devices.

Although some embodiments may be illustrated and described as comprising functional components, software, engines, and/or modules performing various operations, it can be appreciated that such components or modules may be implemented by one or more hardware components, software components, and/or combination thereof. The functional components, software, engines, and/or modules may be implemented, for example, by logic (e.g., instructions, data, and/or code) to be executed by a logic device (e.g., processor). Such logic may be stored internally or externally to a logic device on one or more types of computer-readable storage media. In other embodiments, the functional components such as software, engines, and/or modules may be implemented by hardware elements that may include processors, microprocessors, circuits, circuit elements (e.g., transistors, resistors, capacitors, inductors, and so forth), integrated circuits, application specific integrated circuits (ASIC), programmable logic devices (PLD), digital signal processors (DSP), field programmable gate array (FPGA), logic gates, registers, semiconductor device, chips, microchips, chip sets, and so forth.

Examples of software, engines, and/or modules may include software components, programs, applications, computer programs, application programs, system programs, machine programs, operating system software, middleware, firmware, software modules, routines, subroutines, functions, methods, procedures, software interfaces, application program interfaces (API), instruction sets, computing code, computer code, code segments, computer code segments, words, values, symbols, or any combination thereof. Determining whether an embodiment is implemented using hardware elements and/or software elements may vary in accordance with any number of factors, such as desired computational rate, power levels, heat tolerances, processing cycle budget, input data rates, output data rates, memory resources, data bus speeds and other design or performance constraints.

In some cases, various embodiments may be implemented as an article of manufacture. The article of manufacture may include a computer readable storage medium arranged to store logic, instructions and/or data for performing various operations of one or more embodiments. In various embodiments, for example, the article of manufacture may comprise a magnetic disk, optical disk, flash memory or firmware containing computer program instructions suitable for execution by a general purpose processor or application specific processor. The embodiments, however, are not limited in this context.

Additionally, it is to be appreciated that the embodiments described herein illustrate example implementations, and that the functional elements, logical blocks, modules, and circuits elements may be implemented in various other ways which are consistent with the described embodiments. Furthermore, the operations performed by such functional elements, logical blocks, modules, and circuits elements may be combined and/or separated for a given implementation and may be performed by a greater number or fewer number of components or modules. As will be apparent to those of skill in the art upon reading the present disclosure, each of the individual embodiments described and illustrated herein has discrete components and features which may be readily separated from or combined with the features of any of the other several aspects without departing from the scope of the present disclosure. Any recited method can be carried out in the order of events recited or in any other order which is logically possible.

Reference to "one embodiment" or "an embodiment" means that a particular feature, structure, or characteristic described in connection with the embodiment is comprised in at least one embodiment. The appearances of the phrase "in one embodiment" or "in one aspect" in the specification are not necessarily all referring to the same embodiment.

Unless specifically stated otherwise, it may be appreciated that terms such as "processing," "computing," "calculating," "determining," or the like, refer to the action and/or processes of a computer or computing system, or similar electronic computing device, such as a general purpose processor, a DSP, ASIC, FPGA or other programmable logic device, discrete gate or transistor logic, discrete hardware components, or any combination thereof designed to perform the functions described herein that manipulates and/or transforms data represented as physical quantities (e.g., electronic) within registers and/or memories into other data similarly represented as physical quantities within the memories, registers or other such information storage, transmission or display devices.

Certain embodiments may be described using the expression "coupled" and "connected" along with their derivatives. These terms are not necessarily intended as synonyms for each other. For example, some embodiments may be described using the terms "connected" and/or "coupled" to indicate that two or more elements are in direct physical or electrical contact with each other. The term "coupled," however, also may mean that two or more elements are not in direct contact with each other, but yet still co-operate or interact with each other. With respect to software elements, for example, the term "coupled" may refer to interfaces, message interfaces, application program interface (API), exchanging messages, and so forth.

The terms "a" and "an" and "the" and similar referents used in the context of the present disclosure (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as when it was individually recited herein. All methods described herein can be performed in any suitable order unless otherwise indicated herein or otherwise clearly contradicted by context. The use of any and all examples, or exemplary language (e.g., "such as," "in the case," "by way of example") provided herein is intended merely to better illuminate the disclosed embodiments and does not pose a limitation on the scope otherwise claimed. No language in the specification should be construed as indicating any non-claimed element essential to the practice of the claimed subject matter. It is further noted that the claims may be drafted to exclude any optional element. As such, this statement is intended to serve as antecedent basis for use of such exclusive terminology as solely, only, and the like in connection with the recitation of claim elements, or use of a negative limitation.

Groupings of alternative elements or embodiments disclosed herein are not to be construed as limitations. Each group member may be referred to and claimed individually or in any combination with other members of the group or other elements found herein. It is anticipated that one or more members of a group may be comprised in, or deleted from, a group for reasons of convenience and/or patentability.

The flow charts and methods described herein show the functionality and operation of various implementations. If embodied in software, each block, step, or action may represent a module, segment, or portion of code that comprises program instructions to implement the specified logical function(s). The program instructions may be embodied in the form of source code that comprises human-readable statements written in a programming language or machine code that comprises numerical instructions recognizable by a suitable execution system such as a processing component in a computer system. If embodied in hardware, each block may represent a circuit or a number of interconnected circuits to implement the specified logical function(s).

It will be appreciated that those skilled in the art will be able to devise various arrangements which, although not explicitly described or shown herein, embody the principles of the present disclosure and are comprised within the scope thereof. Furthermore, all examples and conditional language recited herein are principally intended to aid the reader in understanding the principles described in the present disclosure and the concepts contributed to furthering the art, and are to be construed as being without limitation to such specifically recited examples and conditions. Moreover, all statements herein reciting principles, aspects, and embodiments as well as specific examples thereof, are intended to encompass both structural and functional equivalents thereof. Additionally, it is intended that such equivalents comprise both currently known equivalents and equivalents developed in the future, i.e., any elements developed that perform the same function, regardless of structure. The scope of the present disclosure, therefore, is not intended to be limited to the exemplary aspects and aspects shown and described herein.

What is claimed is:

1. A modeling system comprising:
    a physical atomic model including:
        a three-dimensional spherical structure representing a nucleus, wherein the three-dimensional structure has primarily one color that is selected from a finite set of colors,
        at least one bonding arm connected to an outer surface of the nucleus structure, wherein the at least one bonding arm extends distally from the nucleus structure,
        a magnetically attractive portion attached to a distal end of the at least one bonding arm, and
        at least one bonding site on the outer surface of the nucleus structure, wherein the at least one bonding site includes a magnet structured for connecting at least one magnetically attractive portion thereto; and
    an application stored on a computer-readable medium, the application including a vision detection and analysis algorithm which when executed by a processor causes the processor to:
        receive image data for a captured image of the physical atomic model,
        from the received image data, identify a first portion of the image having one of the finite set of colors,
        identify at least one contour in the first portion of the image,
        estimate a size of an object in the first portion of the image based on the identified at least one contour, and
        identify an atom represented by the object based on the estimated size of the object and the color of the first portion of the image.

2. The modeling system of claim 1, wherein at least one aspect of the atomic model is marked with at least one indicia indicating a type of atom represented by the atomic model.

3. The modeling system of claim 2, wherein the indicia is displayed on the nucleus structure of the atomic model and the indicia is complementarily colored, contrastingly colored, or colored differently than the primary color of the nucleus structure.

4. The modeling system of claim 1, wherein a weight of the nucleus structure is related to an atomic weight of the atom represented by the atomic model.

5. The modeling system of claim 1, wherein a size of the nucleus structure is related to a period of a periodic table of elements.

6. The modeling system of claim 1, wherein at least one bonding site is highlighted with a visually perceptible indicia.

7. The modeling system of claim 1, wherein the application includes instructions which when executed by the processor cause the processor to compare at least one aspect of the atomic model to a database including atomic information.

8. The modeling system of claim 7, wherein the application includes instructions which when executed by the processor cause the processor to present information to a user about at least one aspect of the atomic model.

9. The modeling system of claim 7, wherein the application includes instructions which when executed by the processor cause the processor to communicate that the atomic model does not match an entry in the database.

10. The modeling system of claim 1, wherein the vision detection and analysis algorithm causes the processor to determine at least one non-black or non-white area associated with the image data.

11. The modeling system of claim 1, wherein the vision detection and analysis algorithm causes the processor to generate a mask based on the image data, wherein the mask includes at least one area which is ignored by atom detection processing of the vision detection and analysis algorithm.

12. The modeling system of claim 1, wherein the vision detection and analysis algorithm causes the processor to execute a best circle fit test for each of the identified contours.

13. The modeling system of claim 1, wherein the vision detection and analysis algorithm causes the processor to combine at least two identified contours and to execute a best circle fit test on the combined contours.

14. The modeling system of claim 1, further comprising a circuit included within the nucleus structure, the circuit configured to activate a switch associated with at least one connection communication means when at least one magnetically attractive portion is connected to at least one bonding site.

15. The modeling system of claim 14, wherein the connection communication means comprises at least one of a lighting means, an audible indication means, a vibration means, or a combination thereof.

16. The modeling system of claim 14, wherein the circuit further comprises at least one switch configured for activation by a magnetic field generated when at least one magnetically attractive portion is connected to at least one bonding site.

17. A modeling system comprising:
a first and a second physical atomic model each including:
a three-dimensional spherical structure representing a nucleus, wherein the three-dimensional spherical structure has primarily one color that is selected from a finite set of colors,
at least one bonding arm connected to an outer surface of the nucleus structure, wherein the at least one bonding arm extends distally from the nucleus structure,
a magnetically attractive portion attached to a distal end of the at least one bonding arm, and
at least one bonding site on the outer surface of the nucleus structure, wherein the at least one bonding site includes a magnet structured for connecting at least one magnetically attractive portion thereto, wherein the magnet of the at least one bonding site of the second physical atomic model is connected to the magnetically attractive portion of the first physical atomic model to form a molecular model comprising the first and second physical atomic models; and
an application stored on a computer-readable medium, the application including a vision detection and analysis algorithm which when executed by a processor causes the processor to:
receive image data for a captured image of the molecular model,
from the received image data, identify a first portion of the image having one of the finite set of colors and a second portion of the image having one of the finite set of colors,
identify a first at least one contour in the first portion of the image and a second at least one contour in the second portion of the image,
estimate a size of a first object in the first portion of the image based on the first identified at least one contour and a size of a second object in the first portion of the image based on the second identified at least one contour, and
identify a first atom represented by the first object and a second atom represented by the second object based on the estimated sizes of the first and second object and the colors of the first and the second portion,
determine an identity of the molecular model based on the identified first and second atom.

18. A modeling system comprising:
at least one physical atomic model including:
a structure representing a nucleus,
at least one bonding arm connected to the nucleus structure,
a magnetically attractive portion attached to a distal end of the bonding arm, and
at least one bonding site including a magnet structured for connecting at least one magnetically attractive portion thereto; and
an application stored on a computer-readable medium, the application including a vision detection and analysis algorithm which when executed by a processor causes the processor to:
capture image data associated with the physical atomic model,
identify at least one color associated with the captured image data,
identify at least one contour associated with the captured image data, and
in response to the identified color and the identified contour, identify at least one atom represented by the physical atomic model; and
a circuit included within the nucleus structure, the circuit configured to activate a switch associated with at least one connection communication means when at least one magnetically attractive portion is connected to at least one bonding site.

* * * * *